United States Patent
Peskar et al.

(10) Patent No.: US 11,452,874 B2
(45) Date of Patent: Sep. 27, 2022

(54) SHAPE CONTROL FOR ELECTRICAL STIMULATION THERAPY

(71) Applicant: Medtronic, Inc., Minneapolis, MN (US)

(72) Inventors: Cheryl Peskar, Woodbury, MN (US); Alicia Weller Thompson, Coon Rapids, MN (US); Susan E. Heilman Kilbane, Deephaven, MN (US); Lance Beall, Andover, MN (US); Brendan J. Young-Dixon, St. Paul, MN (US); Rebecca A Miron, Center City, MN (US); Rebecca J. S. Haag, Broomfield, CO (US)

(73) Assignee: Medtronic, Inc., Minneapolis, MN (US)

( * ) Notice: Subject to any disclaimer, the term of this patent is extended or adjusted under 35 U.S.C. 154(b) by 137 days.

(21) Appl. No.: 16/780,633

(22) Filed: Feb. 3, 2020

(65) Prior Publication Data
US 2021/0236823 A1 Aug. 5, 2021

(51) Int. Cl.
*A61N 1/36* (2006.01)
*A61N 1/02* (2006.01)
(Continued)

(52) U.S. Cl.
CPC ......... *A61N 1/36185* (2013.01); *A61N 1/025* (2013.01); *A61N 1/36171* (2013.01);
(Continued)

(58) Field of Classification Search
CPC .... A61N 1/025; A61N 1/0531; A61N 1/0534; A61N 1/36171; A61N 1/36175;
(Continued)

(56) References Cited

U.S. PATENT DOCUMENTS

| 5,306,292 | A | 4/1994 | Lindegren |
| 5,626,629 | A | 5/1997 | Faltys et al. |

(Continued)

FOREIGN PATENT DOCUMENTS

| CN | 105209111 A | 12/2015 |
| EP | 1181951 B1 | 3/2004 |

(Continued)

OTHER PUBLICATIONS

"Arrhythmia: Heart Palpitations." Cleveland Clinic, http://my.clevelandclinic.org/heart/disorders/electric/palpitations.aspx, captured Mar. 5, 2010, 2 pp.

(Continued)

*Primary Examiner* — Carl H Layno
*Assistant Examiner* — Jane C Kalinock
(74) *Attorney, Agent, or Firm* — Shumaker & Sieffert, P.A.

(57) ABSTRACT

Devices, systems, and techniques are described for adjusting therapy parameters defining electrical stimulation therapy delivered by multiple electrodes while maintaining a ratio of a value of a therapy parameter between the multiple electrodes. In one example, a device defines a relationship for multiple electrodes that defines a ratio of a value of a therapy parameter between the multiple electrodes. The device performs a master adjustment that adjusts each value of the therapy parameter for each respective electrode of the multiple electrodes by an amount specified by the relationship to maintain the ratio of the value of the therapy parameter between the multiple electrodes. The device controls delivery of electrical stimulation therapy according to the master adjustment.

20 Claims, 11 Drawing Sheets

(51) Int. Cl.
*A61N 1/372* (2006.01)
*A61N 1/05* (2006.01)

(52) U.S. Cl.
CPC ..... *A61N 1/36175* (2013.01); *A61N 1/37247* (2013.01); *A61N 1/0531* (2013.01); *A61N 1/0534* (2013.01)

(58) Field of Classification Search
CPC .. A61N 1/36185; A61N 1/37247; A61N 1/05; A61N 1/08; A61N 1/36146
USPC .......................................................... 607/59
See application file for complete search history.

(56) References Cited

U.S. PATENT DOCUMENTS

| | | |
|---|---|---|
| 5,775,331 A | 7/1998 | Raymond et al. |
| 5,928,272 A | 7/1999 | Adkins et al. |
| 6,259,945 B1 | 7/2001 | Epstein et al. |
| 6,393,325 B1 | 5/2002 | Mann et al. |
| 6,473,644 B1 | 10/2002 | Terry, Jr. et al. |
| 6,587,724 B2 | 7/2003 | Mann |
| 6,622,048 B1 | 9/2003 | Mann et al. |
| 6,640,136 B1 | 10/2003 | Helland et al. |
| 6,731,986 B2 | 5/2004 | Mann |
| 7,065,412 B2 | 6/2006 | Swoyer et al. |
| 7,104,965 B1 | 9/2006 | Jiang et al. |
| 7,174,215 B2 | 2/2007 | Bradley |
| 7,254,446 B1 | 8/2007 | Erickson et al. |
| 7,317,944 B1 | 1/2008 | Overstreet |
| 7,317,948 B1 | 1/2008 | King et al. |
| 7,499,752 B2 | 3/2009 | Machino et al. |
| 7,519,431 B2 | 4/2009 | Goetz et al. |
| 7,567,840 B2 | 7/2009 | Armstrong |
| 7,578,819 B2 | 8/2009 | Bleich et al. |
| 7,643,881 B2 | 1/2010 | Armstrong |
| 7,689,286 B2 | 3/2010 | Pastore et al. |
| 7,711,419 B2 | 5/2010 | Armstrong et al. |
| 7,768,151 B2 | 8/2010 | Andreu et al. |
| 8,055,337 B2 | 11/2011 | Moffitt et al. |
| 8,560,080 B2 | 10/2013 | Goetz et al. |
| 8,738,145 B2 | 5/2014 | Goetz et al. |
| 8,825,169 B2 | 9/2014 | Zhu et al. |
| 8,996,123 B2 | 3/2015 | Goetz et al. |
| 9,358,390 B2 | 6/2016 | Polefko et al. |
| 9,649,494 B2 | 5/2017 | Gerber et al. |
| 9,764,147 B2 | 9/2017 | Torgerson |
| 9,789,307 B2 | 10/2017 | Gerber et al. |
| 9,913,975 B2 | 3/2018 | Carbunaru et al. |
| 10,448,889 B2 | 10/2019 | Gerber et al. |
| 2002/0072770 A1 | 6/2002 | Pless |
| 2003/0073899 A1 | 4/2003 | Ruohonen et al. |
| 2003/0153959 A1 | 8/2003 | Thacker et al. |
| 2004/0098063 A1 | 5/2004 | Goetz |
| 2004/0116978 A1 | 6/2004 | Bradley |
| 2004/0158298 A1 | 8/2004 | Gliner et al. |
| 2004/0167586 A1 | 8/2004 | Overstreet |
| 2005/0107654 A1 | 5/2005 | Riehl |
| 2005/0119714 A1 | 6/2005 | Sieracki et al. |
| 2005/0222626 A1 | 10/2005 | DiLorenzo |
| 2005/0245987 A1 | 11/2005 | Woods et al. |
| 2006/0074450 A1 | 4/2006 | Boveja et al. |
| 2006/0085048 A1 | 4/2006 | Cory et al. |
| 2006/0167498 A1 | 7/2006 | DiLorenzo |
| 2006/0173510 A1 | 8/2006 | Besio et al. |
| 2006/0195159 A1 | 8/2006 | Bradley et al. |
| 2006/0229677 A1 | 10/2006 | Moffitt et al. |
| 2006/0253174 A1 | 11/2006 | King |
| 2007/0016097 A1 | 1/2007 | Farquhar et al. |
| 2007/0043395 A1 | 2/2007 | Wei et al. |
| 2007/0100389 A1 | 5/2007 | Jaax et al. |
| 2007/0233194 A1 | 10/2007 | Craig |
| 2007/0255320 A1 | 11/2007 | Inman et al. |
| 2008/0027514 A1 | 1/2008 | DeMulling et al. |
| 2008/0086175 A1 | 4/2008 | Libbus et al. |
| 2008/0109048 A1 | 5/2008 | Moffitt |
| 2008/0147140 A1 | 6/2008 | Ternes et al. |
| 2008/0221637 A1 | 9/2008 | Woods et al. |
| 2008/0234780 A1 | 9/2008 | Smith et al. |
| 2008/0269812 A1 | 10/2008 | Gerber et al. |
| 2008/0281381 A1 | 11/2008 | Gerber et al. |
| 2009/0030493 A1 | 1/2009 | Colborn et al. |
| 2009/0043352 A1 | 2/2009 | Brooke et al. |
| 2009/0076561 A1 | 3/2009 | Libbus et al. |
| 2009/0112281 A1 | 4/2009 | Miyazawa et al. |
| 2009/0149917 A1 | 6/2009 | Whitehurst et al. |
| 2009/0198294 A1 | 8/2009 | Rossing et al. |
| 2009/0299214 A1 | 12/2009 | Wu et al. |
| 2010/0010383 A1 | 1/2010 | Skelton et al. |
| 2010/0010390 A1 | 1/2010 | Skelton et al. |
| 2010/0010576 A1 | 1/2010 | Skelton et al. |
| 2010/0010580 A1 | 1/2010 | Skelton et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0030299 A1 | 2/2010 | Covalin |
| 2010/0114192 A1 | 5/2010 | Jaax et al. |
| 2010/0114204 A1 | 5/2010 | Burnes et al. |
| 2010/0114221 A1 | 5/2010 | Krause et al. |
| 2010/0121408 A1 | 5/2010 | Imran et al. |
| 2010/0121409 A1 | 5/2010 | Kothandaraman et al. |
| 2010/0161007 A1 | 6/2010 | King |
| 2010/0106219 A1 | 8/2010 | Torgerson et al. |
| 2010/0249875 A1 | 9/2010 | Kishawi et al. |
| 2010/0262209 A1 | 10/2010 | King et al. |
| 2011/0046506 A1 | 2/2011 | Durand et al. |
| 2011/0270119 A1 | 11/2011 | Rasmussen |
| 2011/0270357 A1 | 11/2011 | Torgerson et al. |
| 2011/0276107 A1 | 11/2011 | Simon et al. |
| 2012/0109004 A1 | 5/2012 | Cadwell |
| 2012/0271382 A1 | 10/2012 | Arcot-Krishnamurthy et al. |
| 2012/0277621 A1 | 11/2012 | Gerber et al. |
| 2013/0131760 A1 | 5/2013 | Rao et al. |
| 2015/0119957 A1* | 4/2015 | Ranu ................. A61N 1/36185 607/66 |
| 2016/0082261 A1 | 3/2016 | Moffitt et al. |
| 2019/0184168 A1 | 6/2019 | Vansickle et al. |

FOREIGN PATENT DOCUMENTS

| | | |
|---|---|---|
| WO | 2004064634 A1 | 8/2004 |
| WO | 2006073393 A1 | 7/2006 |
| WO | 2009134478 A1 | 11/2009 |
| WO | 2009158389 A1 | 12/2009 |
| WO | 2010065146 A1 | 6/2010 |
| WO | 2010105261 A1 | 9/2010 |

OTHER PUBLICATIONS

"Bradycardia (Slow Heart Rate)—Overview" WebMD, http://www.webmd.com/heart-disease/tc/bradycardia-slow-heart-rate-overview, captured Jan. 30, 2010, updated Jun. 18, 2009, 2 pp.

Schachter et al., "Warning Signs of Seizures," Aug. 2013, Epilepsy Foundation, retrieved from internet www.epilepsy.com/get-help/managing-your-epilepsy/understanding-seizures-and-emergencies/warning-signs-seizures on Dec. 15, 2014, 2 pp.

U.S. Appl. No. 16/595,195, filed Oct. 7, 2019 by Gerber et al.

U.S. Appl. No. 16/694,549, filed Nov. 25, 2019 by Young-Dixon et al.

International Search Report and Written Opinion of International Application No. PCTIUS2021/015860, dated Apr. 26, 2021, 15 pp.

* cited by examiner

SHAPE CONTROL FOR ELECTRICAL STIMULATION THERAPY

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. The electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, epilepsy, urinary or fecal incontinence, pelvic pain, sexual dysfunction, obesity, or gastroparesis. An electrical stimulator may be configured to deliver electrical stimulation therapy via leads that include electrodes proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

SUMMARY

In general, the disclosure describes devices, systems, and techniques for maintaining ratios of therapy parameter values between multiple electrodes when adjusting the therapy parameters. The therapy parameters may define electrical stimulation delivered by each of the electrodes. In one example, a device, such as an external programmer for an implantable medical device, defines a relationship for one or more therapy parameters for multiple electrodes of a plurality of electrodes of the implantable medical device. The relationship may define a ratio of values for a therapy parameter of multiple electrodes. In this manner, the ratio may be set between one or more electrodes and another one or more electrodes. The therapy parameter may at least partially define electrical stimulation delivered via the electrode and may include, e.g., a current amplitude, a voltage amplitude, an electrical stimulation pulse count, a frequency, a pulse width, etc.

When two or more electrodes have been "locked" into a ratio for a therapy parameter, the device can perform a master adjustment to adjust each value of the therapy parameters of each of multiple electrodes by an amount specified by the relationship to maintain the ratio of the values of the therapy parameters for the multiple electrodes. The device can therefore control delivery of electrical stimulation therapy according to the master adjustment.

In some examples, the device presents, for display to a user, a user interface including a representation of the plurality of electrodes. The user interface may depict, e.g., values of the therapy parameters specific to each of the plurality of electrodes, a selection of the multiple electrodes for which the relationship is defined, a value of a master adjustment to the selected multiple electrodes, etc. The user interface may further depict a representation of a status of the relationship. For example, the user interface may indicate whether the relationship for the multiple electrodes is "locked." When locked, the user may request, via the user interface, the device to make a master adjustment to the therapy parameters for each of the selected electrodes so as to maintain the ratio of the values of the therapy parameters of the multiple electrodes. Additionally, the user interface may indicate whether the relationship for the multiple electrodes is "unlocked." When unlocked, the user may request, via the user interface, that the device adjusts values of individual therapy parameters for specific electrodes of the plurality of electrodes without maintaining any relationship for the therapy parameter values between the electrodes.

The techniques of the disclosure may provide specific improvements to the computer-related field of neurostimulation therapy that have practical applications. For example, the techniques described herein enable a user interface that enables a clinician to define a shape of an electrical field generated by electrical stimulation therapy. Further, the techniques described herein enable a user interface that enables a clinician to adjust one or more parameter values of the electrical stimulation therapy while maintaining a desired shape of the electrical field generated by the electrical stimulation therapy. For example, electrodes locked into a relationship of parameter values may preserve that desired shape of the electrical field when changing an amplitude of stimulation. In this manner, the techniques of the disclosure may describe a user interface that enables a clinician to easily define highly complex configurations of electrical stimulation therapy while simplifying the adjustment of individual parameters for each electrode of the electrical stimulation therapy through a specified therapy parameter relationship between electrodes. Accordingly, by using the techniques set forth herein, a medical device may deliver electrical stimulation therapy that is highly tailored to a specific patient so as to increase the therapeutic efficacy of the electrical stimulation therapy as well as reduce the occurrence and/or severity of side-effects of the electrical stimulation therapy.

In one example, this disclosure describes a method comprising: defining, by processing circuitry, a relationship for multiple electrodes of a plurality of electrodes, wherein the relationship defines a ratio of a value of a therapy parameter between the multiple electrodes; performing, by the processing circuitry, a master adjustment that adjusts each value of the therapy parameter for each respective electrode of the multiple electrodes by an amount specified by the relationship to maintain the ratio of the value of the therapy parameter between the multiple electrodes; and controlling, by the processing circuitry, delivery of electrical stimulation according to the master adjustment.

In another example, this disclosure describes a system comprising: a memory; and processing circuitry operatively coupled to the memory and configured to: define a relationship for multiple electrodes of a plurality of electrodes, wherein the relationship defines a ratio of a value of a therapy parameter between the multiple electrodes; perform a master adjustment that adjusts each value of the therapy parameter for each respective electrode of the multiple electrodes by an amount specified by the relationship to maintain the ratio of the value of the therapy parameter between the multiple electrodes; and control delivery of electrical stimulation according to the master adjustment.

In another example, this disclosure describes a device comprising: a display; a memory; and processing circuitry operatively coupled to the memory and configured to: control the display to output, for display to a user, a representation of a plurality of electrodes; receive a first input specifying a selection of multiple electrodes of the plurality of electrodes; control the display to output, for display to the user and in response to receiving the first input, a representation of the selected multiple electrodes; receive a second input specifying a value of a therapy parameter of each electrode of the multiple electrodes; control the display to output, for display to the user and in response to receiving the second input, a representation of the value of the therapy parameter of each electrode of the multiple electrodes; receive a third input to lock a relationship for the selected multiple electrodes of the plurality of electrodes, wherein the relationship defines a ratio of a value of a therapy parameter between the multiple electrodes; control the display to output, for display to the user and in response to receiving the third input, an indication that the relationship for the selected multiple electrodes of the plurality of electrodes is locked; receive a fourth input specifying a master adjustment that adjusts each value of the therapy parameter for each respective electrode of the selected multiple electrodes by an amount specified by the relationship to maintain the ratio of the value of the therapy parameter between the multiple electrodes; and control the display to output, for display to the user and in response to receiving the fourth input, a representation of the master adjustment to the values of the therapy parameters of the multiple electrodes.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description

DETAILED DESCRIPTION

Figure 1:
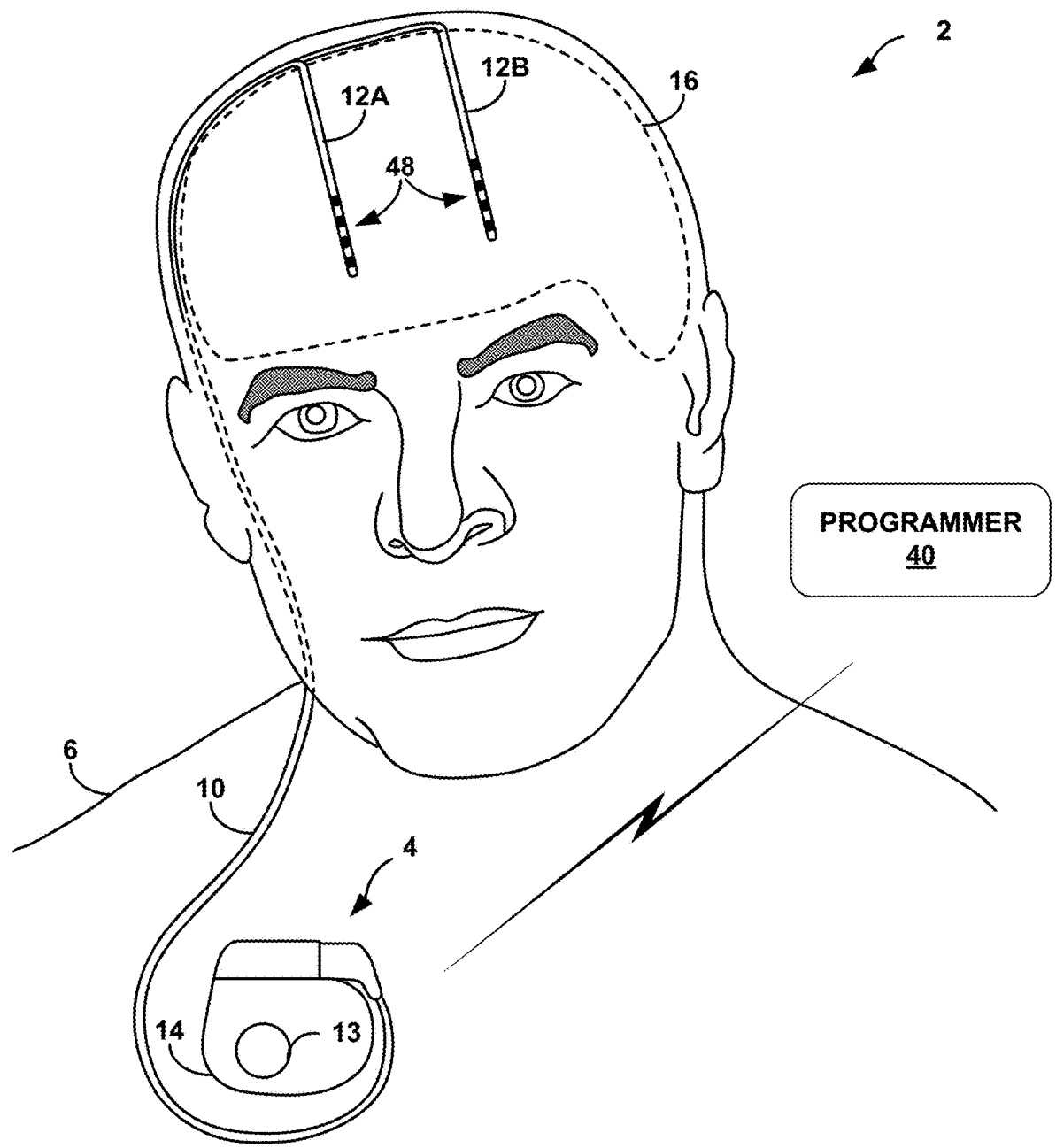
FIG. 1 is a conceptual diagram illustrating an example therapy system that includes an electrical stimulator coupled to a stimulation lead, in accordance with various techniques of this disclosure.

Devices, systems, and techniques are described herein for maintaining ratios of therapy parameter values between multiple electrodes when adjusting a therapy parameter. When programming Deep Brain Stimulation (DBS) therapy, a clinician can specify an electrode configuration and then define delivery of electrical stimulation via the electrode configuration by assigning values of one or more therapy parameters to individual electrodes and/or adjusting values of these therapy parameters. A clinician typically assigns a value by, for example, assigning a single amplitude value to all active electrodes or allocating a percentage of a single overall amplitude to each electrode to achieve multiple distinct amplitude values for respective electrodes. This electrode-specific approach to programming can be cumbersome, inefficient, and time consuming for the clinician, particularly when programming more complex electrode configurations. For example, if a clinician desires to adjust the overall size of the stimulation field or the overall size of a particular region of the stimulation field, the clinician may need to manually adjust the amplitude values for each electrode associated with the desired change.

Devices, systems, and techniques are disclosed herein for programming therapy parameters that enable a user to control or adjust stimulation settings (such as stimulation amplitude) for selections of multiple electrodes at the same time. The techniques described herein provide software user interface (UI) elements or other user interface devices enabled to receive user input that requests the system to virtually "lock" a desired grouping of electrodes together and proportionally increase or decrease values of stimulation parameters simultaneously, thereby adjusting the entire stimulation field as a whole. The lock may apply to one or more of the parameters that define electrical stimulation.

For example, the grouping of electrodes may include two or more active electrodes, and a clinician may adjust the values for the therapy parameters for the grouping of electrodes together as a batch/group, either on a single lead ring level (e.g. a level control circle which may correlate to all of the electrodes located at the same axial position along the lead) or an entire stimulation field shape. The user may lock the electrodes together through the use of a selectable "lock" button of a user interface for programming the medical device. The user interface may further include elements (e.g., selectable buttons, input fields, etc.) that are configured to receive user input requesting adjustment to the values of one or more stimulation parameters of multiple electrodes at the same time (e.g., master amplitude slider, patient limit flags). The user interface may further present a volume of neural activation (VNA) model that depicts the increase or decrease of the stimulation field shape as a result of any changes to stimulation parameters. Furthermore, the techniques disclosed herein enable a medical device to display, to the user, any changes to the stimulation field shape via a representation of the therapy parameters and selected electrodes displayed on a screen of the medical device. The techniques described herein for setting and adjusting stimulation parameters may reduce the complexity and increase the efficiency of the programming experience for the user.

FIG. 1 is a conceptual diagram illustrating example therapy system 2 that includes electrical stimulator 4 coupled to stimulation lead 10, in accordance with various techniques of this disclosure. Therapy system 2 may be configured to deliver stimulation therapy to patient 6. Patient 6 ordinarily, but not necessarily, will be a human. Generally, therapy system 2 includes electrical stimulator 4 (e.g., an implantable medical device (IMD)) that delivers electrical stimulation to patient 6 via one or more electrodes disposed on stimulation lead extension 10. Electrical stimulator 4 delivers stimulation therapy, e.g., in the form of electrical stimulation, via one or more electrodes 48 disposed along one or more medical leads 12A and 12B which connect to lead extension 10. For purposes of description electrodes 48 are described as being implantable electrodes. However, the example techniques are not limited to implantable electrodes.

Electrodes 48 may be deployed on one or more medical leads, such as medical leads 12A and 12B, and in some cases on a housing electrode. The electrical stimulation may be in the form of controlled current pulses or voltage pulses, or substantially continuous current or voltage waveforms. A stimulation program may define various parameters of the pulses or waveforms. The pulses or waveforms may be delivered substantially continuously or in bursts, segments, or patterns, and may be delivered alone or in combination with pulses or waveforms defined by one or more other stimulation programs. In some examples, one or more of the electrodes may be located on a housing 14 of the electrical stimulator 4. In addition, implantable electrodes may be deployed on a leadless stimulator.

In some examples, electrical stimulator 4 may deliver, for example, deep brain stimulation (DBS) or cortical stimulation (CS) therapy to patient 6 via the electrodes carried by lead 12. Although FIG. 1 shows a particular stimulation environment (e.g., DBS), the techniques of this disclosure are not so limited, and electrical stimulator 4 may deliver stimulation therapy to other parts of patient 6, such as the spinal cord of patient 6 as described in U.S. Pat. No. 8,560,080, entitled, "PROGRAMMING TECHNIQUES FOR CONTROLLING RATE OF CHANGE OF ELECTRICAL STIMULATION THERAPY," by Goetz et al, and U.S. Pat. No. 8,996,123, entitled, "MANAGING ELECTRICAL STIMULATION THERAPY BASED ON VARIABLE ELECTRODE COMBINATIONS," by Goetz et al, the contents of which are incorporated by reference herein in their entirety. For example, other electrical stimulation systems may be configured to deliver electrical stimulation to gastrointestinal organs, pelvic nerves or muscle, peripheral nerves, or other stimulation sites. In addition, although FIG. 1 shows a fully implantable electrical stimulator 4, techniques described in this disclosure may be applied to external stimulators having electrodes deployed via percutaneous leads.

In the example illustrated in FIG. 1, electrical stimulator 4 is implanted in a clavicle region of patient 6. Electrical stimulator 4 generates programmable electrical stimulation (e.g., a current or voltage waveform or current or voltage pulses) and delivers the stimulation via a medical lead 10 carrying an array of stimulation electrodes 48. In general, delivery of electrical stimulation using controlled current pulses will be described in this disclosure for purposes of illustration. In some cases, electrical stimulator may include multiple leads. In the example of FIG. 1, a distal end of lead 10 is bifurcated and includes two leads 12A and 12B (collectively "leads 12"). Leads 12A and 12B each include a set of electrodes forming part of the array of electrodes 48. In various examples, leads 12A and 12B may each carry four, eight, or sixteen electrodes. In FIG. 1, each lead 12A, 12B carries four electrodes, configured as ring electrodes at different axial positions near the distal ends of the leads 12.

In other examples, one or more of leads 12A or 12B may include a different array of electrodes. For example, lead 12A may include electrodes at different positions around the perimeter of the lead. In one example, three, four, or more electrodes may be at the same axial position but different circumferential positions around the lead. These electrodes at different circumferential positions may be referred to as "segmented electrodes" because they represent "segments" of a ring around the lead. These electrodes at the same axial position may be referred to as being disposed at the same "level" of the lead. In some examples, a lead may include one or more levels of multiple electrodes and may include one or more complete ring (or cylindrical electrodes) in addition to the one or more levels of multiple electrodes. An example lead may include, from proximal to distal end of the lead, a proximal ring electrode, a first level of three electrodes, a second level of three electrodes, and a distal ring electrode. In other examples, a lead may include four levels of electrodes, where each level has two, three, four, or more electrodes. The electrodes may be circumferentially aligned or offset between levels.

FIG. 1 further depicts a housing electrode 13. Housing electrode 13 may be formed integrally with an outer surface of hermetically-sealed housing 14 of electrical stimulator 4, or otherwise coupled to housing 14. In one example, housing electrode 13 may be described as an active, non-detachable electrode on electrical stimulator 4. In some examples, housing electrode 13 is defined by an uninsulated portion of an outward facing portion of housing 14 of electrical stimulator 4. Other divisions between insulated and uninsulated portions of housing 14 may be employed to define two or more housing electrodes. In some examples, housing electrode 13 comprises substantially all of housing 14, one side of housing 14, a portion of housing 14, or multiple portions of housing 14.

In some examples, electrical stimulator 4 may be coupled to one or more leads which may or may not be bifurcated. In such examples, the leads may be coupled to electrical stimulator 4 directly or via a common lead extension (such as lead extension 10) or separate lead extensions. A proximal end of lead extension 10 may be coupled to a header on electrical stimulator 4. Conductors in the lead body may electrically connect stimulation electrodes located on leads 12 to electrical stimulator 4. Lead extension 10 traverses from the implant site of electrical stimulator 4 along the neck of patient 6 before coupling to leads 12A and 12B. Leads 12A and 12B continue to traverse to the brain 16 of patient 6. In some examples, leads 12A and 12B may be implanted within the right and left hemispheres, respectively, in order to deliver electrical stimulation to one more regions of brain 16.

Leads 12A, 12B may be implanted within a desired location of brain 16 through respective holes in the cranium of patient 6. Leads 12A, 12B may be placed at any location within brain 16 such that the electrodes located on leads 12A, 12B are capable of providing electrical stimulation to targeted tissue. The electrodes of leads 12A, 12B are shown as ring electrodes. In some examples, the electrodes of leads 12A, 12B may have different configurations. For example, the electrodes of leads 12A, 12B may have a complex electrode array geometry that is capable of producing shaped electrical fields. The complex electrode array geometry may include multiple electrodes (e.g., partial ring or electrode "segments") around the perimeter of each leads 12A, 12B. In some examples, leads 12 may have shapes other than elongated cylinders as shown in FIG. 1. For example, leads 12 may be paddle leads, spherical leads, bendable leads, or any other type of shape effective in treating patient 6. In addition, the electrodes may be electrode pads on a paddle lead, circular electrodes surrounding the body of a lead, conformable electrodes, cuff electrodes, segmented electrodes, or any other type of electrodes capable of forming unipolar, bipolar, multi-polar, etc. electrode configurations.

In some examples, electrical stimulator 4 delivers stimulation according to a group of programs at a given time. Each program of such a program group may include respective values for each of a plurality of therapy parameters. The therapy parameters may include, e.g., one of a current or a voltage amplitude, a pulse width, a pulse shape, a pulse rate or pulse frequency, a number of pulses, or an electrode configuration (e.g., electrode combination and polarity). Electrical stimulator 4 may interleave pulses or other signals according to the different programs of a program group. In such examples, programmer 40 may be used to create programs, and assemble the programs into program groups. In some examples, programmer 40 may be used to adjust stimulation parameters of one or more programs of a program group, and select a program group as the current program group to control delivery of stimulation by electrical stimulator 4.

Generally, system 2 delivers stimulation therapy to patient 6 in the form of constant current or voltage waveforms or constant current or voltage pulses. The shapes of the pulses may vary according to different design objectives, and may include ramped or trapezoidal pulses, sinusoidal or otherwise curved pulses, stepped pulses having two or more discrete amplitudes, closely spaced pairs of pulses, and biphasic (positive and negative aspects within a single pulse) or monophasic (only positive or only negative aspects within a single pulse) variations of any of the above. In the case of current-based stimulation, electrical stimulator 4 regulates current that is sourced or sunk by one or more electrodes, referred to as regulated electrodes. In some examples, one or more of the electrodes may be unregulated. In such configurations, the housing electrode and/or a lead electrode may be the unregulated electrode.

A source current may refer to a positive current that flows out of an electrode (anode), whereas a sink current may refer to a negative current that flows into an electrode (cathode). Regulated source currents may sum to produce a greater overall source current (e.g., currents from a plurality of source currents sum together to generate the overall source current). Likewise, regulated sink currents may sum to produce a greater overall sink current (e.g., currents from a plurality of sink currents sum together to generate the overall sink current). Regulated source and regulated sink currents may partially or entirely cancel one another, producing a net difference in the form of a net source current or sink current in the case of partial cancellation. In some examples, an unregulated current path can source or sink current approximately equal to this net difference. In some examples, regulated source and sink currents may be substantially balanced.

In some example implementations (e.g., bipolar/multipolar arrangements), one or more electrodes 48 may be configured to act as anodes and source current while one or more different electrodes 48 may be configured to act as cathodes and sink current. In another example implementation (e.g., unipolar arrangements), housing electrode 13 may be configured to act as an anode and source current while one or more electrodes 48 on one or more leads are configured to act as cathodes and sink current. The techniques of this disclosure may be implemented using, e.g., unipolar arrangements or bipolar/multipolar arrangements.

Therapy system 2 may include a programmer 40, such as an external programmer operated by a clinician or patient. In some examples, a programmer 40 may be a handheld computing device that permits a clinician to program stimulation therapy for patient 6 via a user interface. For example, using programmer 40, the clinician may specify stimulation parameters for use in delivery of stimulation therapy. Programmer 40 may support telemetry with electrical stimulator 4 to download programs and, optionally, upload operational or physiological data stored by electrical stimulator 4. Programmer 40 may also include a display and input keys to allow patient 6 or a clinician to interact with programmer 40 and electrical stimulator 4. In this manner, programmer 40 provides patient 6 with a user interface for control of the stimulation therapy delivered by electrical stimulator 4. For example, patient 6 may use programmer 40 to start, stop or adjust electrical stimulation. In particular, programmer 40 may permit patient 6 to adjust stimulation parameters of a program, such as duration, current or voltage amplitude, pulse width, pulse shape, and pulse rate. Patient 6 may also select a program (e.g., from among a plurality of stored programs) as the present program to control delivery of stimulation by electrical stimulator 4.

In some cases, programmer 40 may be characterized as a physician or clinician programmer 40. For example, programmer 40 may include a clinician programmer if programmer 40 is primarily intended for use by a physician or clinician. In other cases, programmer 40 may be characterized as a patient programmer if programmer 40 is primarily intended for use by a patient. In general, a physician or clinician programmer may support selection and generation of programs by a clinician for use by stimulator 4, whereas a patient programmer may support, during ordinary use, adjustment and selection by a patient of such programs as allowed by the clinician and/or clinician programmer.

Whether programmer 40 is configured for clinician or patient use, programmer 40 may communicate with electrical stimulator 4 or any other computing device via wireless communication. Programmer 40, for example, may communicate via wireless communication with electrical stimulator 4 using RF telemetry techniques known in the art. Programmer 40 may also communicate with another programmer or computing device via a wired or wireless connection using any of a variety of local wireless communication techniques, such as radio frequency (RF) communication according to the 802.11 or Bluetooth specification sets, infrared communication according to the Infrared Data Association (IrDA) specification set, or other standard or proprietary telemetry protocols. Programmer 40 may also communicate with another programming or computing device via exchange of removable media, such as magnetic or optical disks, or memory cards or sticks. Further, programmer 40 may communicate with electrical stimulator 4 and other programming devices via remote telemetry techniques known in the art, communicating via a local area network (LAN), wide area network (WAN), public switched telephone network (PSTN), or cellular telephone network, for example.

A user, such as a clinician or patient 6, may interact with a user interface of programmer 40 to program electrical stimulator 4. In accordance with various techniques described in this disclosure, programmer 40 may be used to receive user input, via the user interface specifying one or more therapy parameters for defining electrical stimulation therapy delivered by electrical stimulator 4. Programmer 40 may control electrical stimulator 4 to cause electrical stimulator 4 to deliver electrical stimulation therapy in accordance with the specified therapy parameters, as described in more detail below, or otherwise program stimulator 4. Programming of electrical stimulator 4 may refer generally to the generation and transfer of commands, programs, or other information to control the operation of electrical stimulator 4. For example, programmer 40 may transmit programs, parameter adjustments, program selections, group selections, or other information to control the operation of electrical stimulator 4. In addition, programming of stimulator 4 may include receiving, via programmer 40, user input indicating a target stimulation zone and controlling the electrical stimulator to transition electrical stimulation from an initial stimulation zone to the target stimulation zone via a sequence of one or more intermediate stimulation zones.

Electrical stimulator 4 and programmer 40 may communicate via cables or a wireless communication, as shown in FIG. 1. Programmer 40 may, for example, communicate via wireless communication with electrical stimulator 4 using RF telemetry techniques. Programmer 40 may also communicate with other programmers using any of a variety of local wireless communication techniques, such as RF communication according to the 802.11 or Bluetooth™ specification sets, infrared communication (e.g., according to the IrDA standard), or other standard or proprietary telemetry protocols. Programmer 40 may include a transceiver to permit bi-directional communication with electrical stimulator 4.

In accordance with the techniques of the disclosure, system 2 enables the adjustment of therapy parameters defining electrical stimulation therapy delivered electrodes 48 while maintaining a ratio of values for each therapy parameter of each of the electrodes 48 to one another. In one example, external programmer 40 defines a relationship for multiple electrodes of a plurality of electrodes 48 of electrical stimulator 4. The relationship defines a ratio of values for a therapy parameter of one or more electrodes to values for the therapy parameter for one or more other electrodes 48. In this manner, if the values change, the ratio of the values for all of the electrodes defined by the relationship will remain constant. The therapy parameter at least partially defines electrical stimulation delivered via the electrode 48 and may include, e.g., a current amplitude, a voltage amplitude, an electrical stimulation pulse count, a frequency, a pulse width, etc. External programmer 40 performs a master adjustment to adjust the value of a therapy parameter for each respective electrode of the multiple electrodes 48 by an amount specified by the relationship to maintain the ratio of the respective values of the therapy parameters of the multiple electrodes 48. External programmer 40 controls electrical stimulator 4 to deliver electrical stimulation therapy to patient 6 in accordance with the master adjustment. The master adjustment may be made in response to user input requesting the adjustment or an automatic adjustment in response to a sensed value or programmed change.

The techniques of the disclosure may provide specific improvements to the computer-related field of neurostimulation therapy that have practical applications. For example, the techniques described herein enable a user interface to define a shape of an electrical field generated by electrical stimulation therapy. Further, the techniques described herein enable a user interface to receive user input requesting an adjust one or more parameters of the electrical stimulation therapy while maintaining a desired shape of the electrical field generated by the electrical stimulation therapy via the relationship of values between at least some of the electrodes. In this manner, the techniques of the disclosure provides a user interface that enables a clinician to easily define highly complex configurations of electrical stimulation therapy, while simplifying the adjustment of individual parameters of the electrical stimulation therapy. Accordingly, by using the techniques set forth herein, a medical device may deliver electrical stimulation therapy that is highly tailored to a specific patient so as to increase the therapeutic efficacy of the electrical stimulation therapy as well as reduce the occurrence and/or severity of side-effects of the electrical stimulation therapy.

Figure 2:
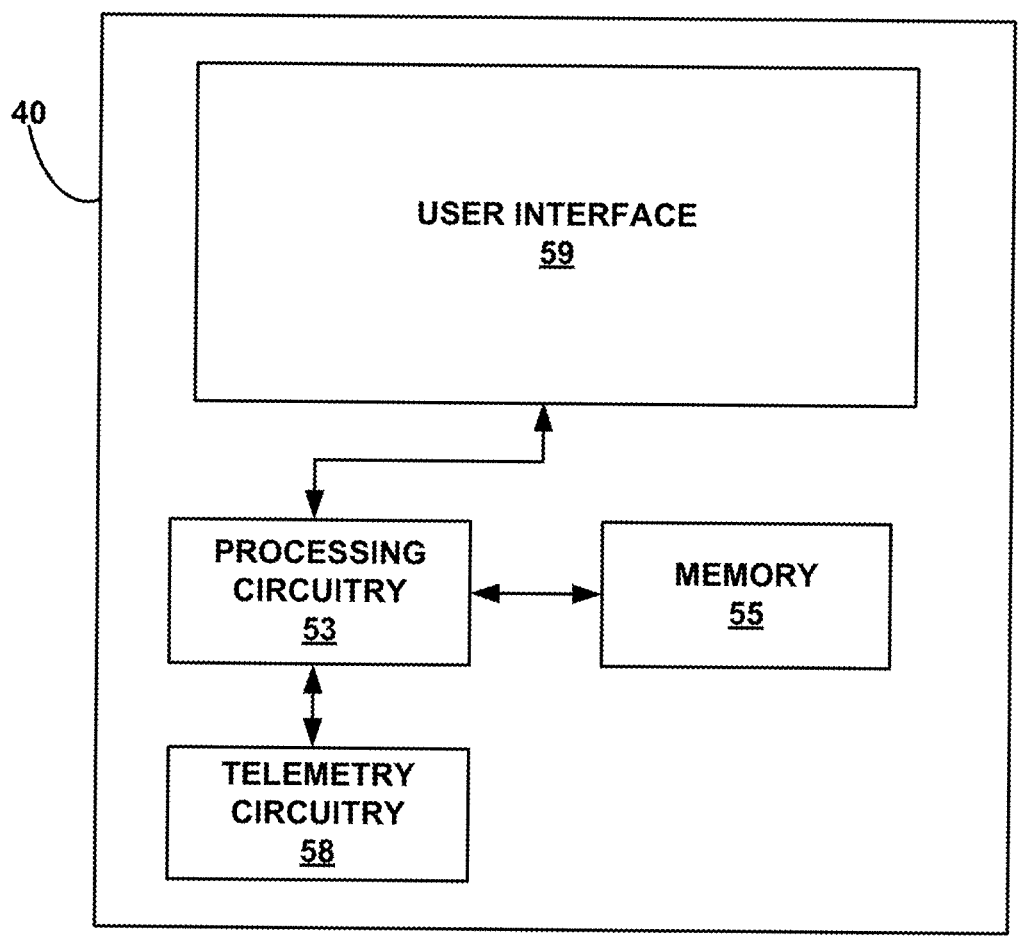
FIG. 2 is a block diagram illustrating the example programmer of FIG. 1 in further detail.

FIG. 2 is a block diagram illustrating example programmer 40 of FIG. 1 in further detail. As shown in FIG. 2, programmer 40 includes processing circuitry 53, memory 55, telemetry circuitry 58, and user interface 59. In general, processing circuitry 53 controls user interface 59, stores and retrieves data to and from memory 55, and controls transmission of data with electrical stimulator 4 through telemetry circuitry 58. Processing circuitry 53 may take the form of one or more microprocessors, controllers, digital signal processors (DSPs), application-specific integrated circuits (ASICs), field-programmable gate arrays (FPGAs), or equivalent discrete or integrated logic circuitry. The functions attributed to processing circuitry 53 herein may be embodied as software, firmware, hardware or any combination thereof.

Memory 55 may store instructions that cause processing circuitry 53 to provide various aspects of the functionality ascribed to programmer 40 herein. Memory 55 may include any fixed or removable magnetic, optical, or electrical media, such as random access memory (RAM), read-only memory (ROM), compact disc ROM (CD-ROM), magnetic memory, electronically-erasable programmable ROM (EEPROM), non-volatile random access memory (NVRAM), flash memory, etc. Memory 55 may also include a removable memory portion that may be used to provide memory updates or increases in memory capacities. A removable memory may also allow patient data to be easily transferred from programmer 40 to another computing device. Memory 55 may also store information that controls operation of electrical stimulator 4.

Telemetry circuitry 58 is configured to transfer data to and from electrical stimulator 4. Telemetry circuitry 58 may communicate automatically with electrical stimulator 4 at a scheduled time or when telemetry circuitry 58 detects the proximity of electrical stimulator 4. Alternatively, telemetry circuitry 58 may communicate with electrical stimulator 4 when signaled by a user through user interface 59. To support RF communication, telemetry circuitry 58 may include appropriate electronic components, such as amplifiers, filters, mixers, encoders, decoders, etc.

In some examples, programmer 40 may communicate wirelessly with electrical stimulator 4 using, for example, RF communication or proximal inductive interaction. This wireless communication is possible through the use of telemetry circuitry 58 which may be coupled to an antenna. Programmer 40 may also be configured to communicate with another computing device via wireless communication techniques, or direct communication through a wired, e.g., network, connection. Examples of local wireless communication techniques that may be employed to facilitate communication between programmer 40 and another computing device include RF communication based on the 802.11 or Bluetooth specification sets, infrared communication.

Programmer 40 includes user interface 59. A user (e.g., a clinician or patient 6) may interact with programmer 40 via user interface 59 to, for example, manually select, change or modify programs, adjust one or more therapy parameters of specific electrodes 48 or a plurality of electrodes 48, or view stimulation data. User interface 59 may comprise one or more input devices and one or more output devices. The input devices of user interface 59 may include a communication device such as a keyboard, pointing device, voice responsive system, video camera, biometric detection/response system, button, sensor, control pad, microphone, presence-sensitive screen, or any other type of device for detecting input from the user.

The output devices of user interface 59 may include a communication unit such as a display, sound card, video graphics adapter card, speaker, presence-sensitive screen, one or more USB interfaces, video and/or audio output interfaces, or any other type of device capable of generating tactile, audio, video, or other output. The output devices of user interface 59 may include a display device, which may function as an output device using technologies including liquid crystal displays (LCD), quantum dot display, dot matrix displays, light emitting diode (LED) displays, organic light-emitting diode (OLED) displays, cathode ray tube (CRT) displays, e-ink, or monochrome, color, or any other type of display capable of generating tactile, audio, and/or visual output. In other examples, the output devices of user interface 59 may produce an output to a user in another fashion, such as via a sound card, video graphics adapter card, speaker, presence-sensitive screen, one or more USB interfaces, video and/or audio output interfaces, or any other type of device capable of generating tactile, audio, video, or other output. In some examples, the output devices of user interface 59 may include a presence-sensitive display that may serve as a user interface device that operates both as one or more input devices and one or more output devices. Additional detail regarding an example of user interface 59 is described with respect to FIGS. 5, 7A-7B, and 8A-8B below.

In accordance with the techniques of the disclosure, user interface 59 presents a representation of the plurality of electrodes 48 of electrical stimulator 4. User interface 59 presents, e.g., values of the therapy parameters specific to each of the plurality of electrodes 48, a selection of the multiple electrodes 48 for which the relationship is defined, a value of a master adjustment to the selected multiple electrodes 48, etc. User interface 59 may provide Tillable fields, or other adjustment input devices, such as increase or decrease input keys, that allow a user to input a desired value for a therapy parameter of a given electrode 48 targeted for adjustment, for multiple electrodes 48 targeted for adjustment, or a master adjustment of electrical stimulator 4. Processing circuitry 53 may receive, from the user via user interface 59, an input specifying adjustments to the values of the individual therapy parameters or the master adjustment by receiving an input specifying an increase or decrease in the corresponding value of the parameter displayed on user interface 59. Further, processing circuitry 53 may receive, from the user, an adjustment to one or more of the therapy parameters corresponding to each particular electrode 48 by receiving an input specifying an increase or decrease in a value of the one or more therapy parameters displayed on the user interface of programmer 40.

User interface 59 may further depict a representation of a status of the relationship. For example, user interface 59 may indicate whether the relationship for the multiple electrodes is "locked," such that the system can perform, in response to a user input request, a master adjustment to the therapy parameters for each of the selected electrodes 48 so as to maintain the ratio of the values of the therapy parameters of the multiple electrodes 48. Additionally, user interface 59 may indicate whether the relationship for the multiple electrodes 48 is "unlocked," such that external programmer 40 may perform, in response to a user request, adjustments to individual therapy parameters for specific electrodes of the plurality of electrodes 48. In some instances, user interface 59 of programmer 40 displays the master adjustment and a fractional amount of the master adjustment associated with each therapy parameter of each electrode 48 of the plurality of electrodes 48 so as to depict the locked relationship of the therapy parameters. In some examples, user interface 59 provides fillable fields, or other adjustment input devices, such as increase or decrease input keys, that allow a user to input a desired value for a therapy parameter of a given electrode 48 targeted for adjustment, for multiple electrodes 48 targeted for adjustment, or the master adjustment. If a user selects one electrode that is locked with other electrodes, processing circuitry 53 may responsively unlock the electrodes in anticipation of the user requesting an adjustment to the individual electrode that was selected.

In operation, processing circuitry 53 receives, from the user via user interface 59, a request to adjust one or more of therapy parameters corresponding to each particular electrode 48. For example, processing circuitry 53 may receive an input specifying an increase or decrease in a value of the one or more therapy parameters displayed on the user interface of programmer 40. Processing circuitry 53 transmits, via telemetry circuitry 58, the specified individual therapy parameters to electrical stimulation 4 to control electrical stimulator 4 to deliver, via multiple electrodes 48, electrical stimulation therapy according to respective therapy parameters of each of the multiple electrodes 48.

Further, processing circuitry 53 receives, in response to an input from a user via user interface 59, an indication to lock a relationship for the multiple electrodes 48 and transmits, to electrical stimulator 4 via telemetry circuitry 58, an instruction to lock a relationship between the multiple electrodes 48. In some examples, by "locking" the relationship of the multiple electrodes, programmer 40 may cause electrical stimulator 4 to "lock" (e.g., maintain or preserve) the ratio of a value of a therapy parameter of each electrode to values of corresponding therapy parameters of each other electrode of the multiple electrodes 48. For example, processing circuitry 53 may receive selections of all of the electrodes to be locked and a selection of a lock icon that submits the request to lock those selected electrodes.

Subsequently, processing circuitry 53 can receive, from the user via user interface 59, an indication of a user input requesting the master adjustment. Processing circuitry 53 controls electrical stimulator 4 to adjust, based on the master adjustment, each value of the therapy parameters of each of the multiple electrodes 48 by an amount specified by the relationship to maintain the ratio of the values of the therapy parameters for the multiple electrodes 48 that are locked together (e.g., all or a subset that is than all of electrodes 48). In this fashion, processing circuitry 53 controls electrical stimulator 4 to adjust a value of a therapy parameter of the electrical stimulation (such as one of a current amplitude or a voltage amplitude, an electrical stimulation pulse count, a frequency, etc.) for a particular electrode 48 while maintaining the relationship of the value of the therapy parameter with respect to the values of corresponding therapy parameters of other electrodes 48. Accordingly, a clinician may use a medical device operating in accordance with the techniques set forth herein to adjust various therapy parameters defining the electrical stimulation therapy so as to optimize therapeutic efficacy of the electrical stimulation therapy as well as reduce the occurrence and/or severity of side-effects of the electrical stimulation therapy.

Figure 3:
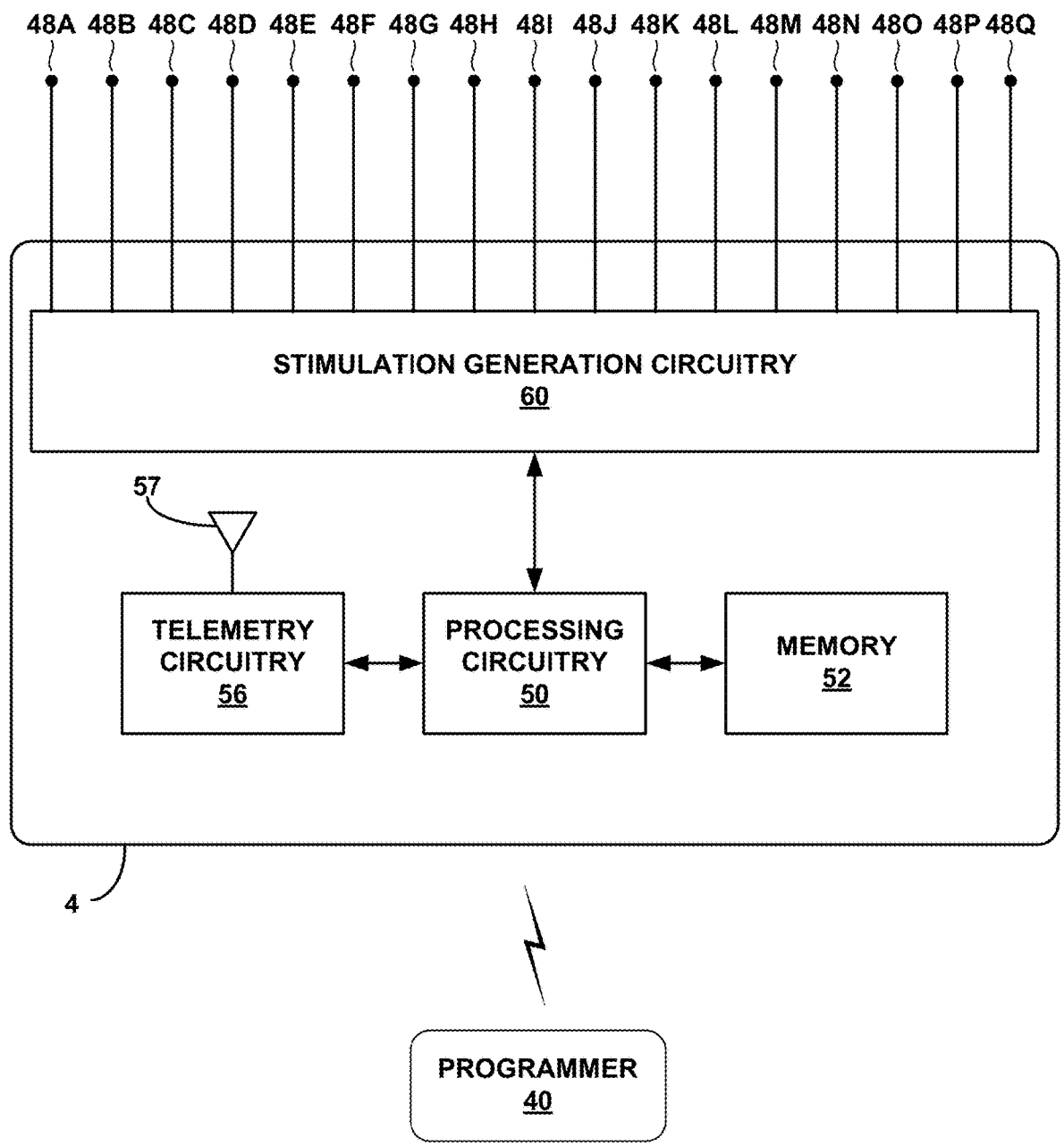
FIG. 3 is a block diagram illustrating the example electrical stimulator of FIG. 1 in further detail.

FIG. 3 is a block diagram illustrating example electrical stimulator 4 of FIG. 1 in further detail. In some examples, electrical stimulator 4 includes processing circuitry 50, memory 52, telemetry circuitry 56, antenna 57, and stimulation generation circuitry 60. Stimulation generation circuitry 60 is also shown in FIG. 3 coupled to electrodes 48A-Q (collectively "electrodes 48"). In some examples, electrodes 48A-48P may be implantable and may be deployed on one or more leads 12. With respect to FIG. 1, leads 12A and 12B may carry electrodes 48A-H and electrodes 48I-P, respectively. In some cases, one or more additional electrodes may be located on or within the housing of electrical stimulator 4, e.g., to provide a common or ground electrode or a housing anode. In some examples, a lead or lead carries eight electrodes to provide a 2×8 electrode configuration (two leads with 8 electrodes each), providing a total of sixteen different electrodes.

In some examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), two or more leads with 11 or 13 electrodes, or other configurations. Processing circuitry 50 may select different electrodes to form various electrode combinations. In addition, processing circuitry 50 may assign various polarities to the selected electrodes to designate the electrodes as anodes or cathodes and form additional electrode configurations therefrom. Fewer or greater electrodes may be controlled by electrical stimulator 4 in other examples. For example, stimulation generation circuitry 60 may be coupled to 16 electrodes, 8 electrodes on each of two leads. For example each lead may include two ring electrodes and two levels of three electrodes at different circumferential positions around the lead perimeter.

Electrode 48Q represents one or more electrodes that may be carried on a housing of electrical stimulator 4. Electrode 48Q may also be a dedicated short lead extending from the housing, or a proximal portion of one of the leads carrying electrodes 48A-48P. The proximal portion may be closely adjacent to the housing, e.g., at or near a point at which a lead is coupled to the housing. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of electrical stimulator 4, such as stimulation generation circuitry 60, processing circuitry 50, memory 52, and telemetry circuitry 56.

Housing electrode 48Q may be configured for use as an anode to source current substantially simultaneously with one or more electrodes 48A-48P configured for use as cathodes sinking current in a unipolar arrangement. By way of specific example, electrodes 48A, 48B, and housing electrode 48Q each could be configured for use as anodes. Electrodes 48A, 48B could deliver electrical stimulation current substantially simultaneously with the electrical stimulation current delivered via housing electrode 48Q. In this illustration, one or more cathodes could be formed with other electrodes (e.g., any of electrodes 48C-48P) on the leads to sink current sourced by anodes 48A, 48B and 48Q.

Memory 52 may store instructions for execution by processing circuitry 50, stimulation therapy data, sensor data, and/or other information regarding therapy for patient 6. Processing circuitry 50 may control stimulation generation circuitry 60 to deliver stimulation according to a selected one or more of a plurality of programs or program groups stored in memory 52. Memory 52 may include any electronic data storage media, such as RAM, ROM, EEPROM, NVRAM, flash memory, magnetic memory, or the like. Memory 52 may store program instructions that, when executed by processing circuitry 50, cause the processing circuitry to perform various functions ascribed to processing circuitry 50 and electrical stimulator 4 in this disclosure.

Processing circuitry 50 may include one or more microprocessors, DSPs, ASICs, FPGAs, or other digital logic circuitry. Processing circuitry 50 controls operation of electrical stimulator 4. For example, processing circuitry 50 may control stimulation generation circuitry 60 to deliver stimulation therapy according to a selected program or group of programs retrieved from memory 52. In some examples, processing circuitry 50 may control stimulation generation circuitry 60 to deliver electrical signals, e.g., as stimulation pulses or continuous waveforms, with current amplitudes, pulse widths (if applicable), and rates specified by one or more stimulation programs. Processing circuitry 50 may also control stimulation generation circuitry 60 to selectively deliver stimulation via subsets of electrodes 48, also referred to as electrode combinations, and with polarities specified by one or more programs. The functions attributed to processing circuitry 50 herein may be embodied as software, firmware, hardware or any combination thereof.

Upon selection of a particular program group, processing circuitry 50 may control stimulation generation circuitry 60 to deliver stimulation according to programs in the groups. Each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. The electrode combination may specify particular electrodes in a single array or multiple arrays, and on a single lead or among multiple leads. The electrode combination may include at least one anode on the housing of the electrical stimulator 4 (e.g., electrode(s) 48Q), at least one anode on a lead, and at least one cathode on a lead. The lead-borne anode and cathode may be on the same lead or different leads, if more than one lead is provided. A program may be defined directly, by selecting parameters and electrodes, or by zone-based programming, in which parameters and electrodes are automatically determined by the programmer in response to manipulation or positioning of stimulation zones.

Stimulation generation circuitry 60 is electrically coupled to electrodes 48A-P via conductors of the respective lead, such as lead 12 in FIG. 1. Stimulation generation circuitry 60 may be electrically coupled to one or more housing electrodes 48Q via an electrical conductor disposed within the housing of electrical stimulator 4. Housing electrode 48Q may be configured as a regulated or unregulated electrode to form an electrode configuration in conjunction with one or more of electrodes 48A-48P. Housing electrode 48Q may be configured for use as an anode to source current substantially simultaneously with one or more electrodes, e.g., any of electrodes 48A-48P, on one or more leads configured for use as anodes.

Stimulation generation circuitry 60 may include stimulation generation circuitry to generate stimulation pulses or waveforms and circuitry for switching stimulation across different electrode combinations, e.g., in response to control by processing circuitry 50. Stimulation generation circuitry 60 produces an electrical stimulation signal in accordance with a program based on control signals from processing circuitry 50.

In one example implementation, stimulation generation circuitry 60 may be configured to deliver stimulation using one or more of electrodes 48A-P and housing electrode 48Q as stimulation electrodes, e.g., anodes. The anodes on the lead(s) and the housing may be used to deliver stimulation in conjunction with one or more cathodes on the lead(s). As one illustration, an electrode combination selected for delivery of stimulation current may comprise a housing anode, and anode on a lead, and a cathode on the same lead or a different lead. In other examples, the electrode combination may include multiple anodes and/or multiple cathodes on one or more leads in conjunction with at least one anode on housing 14. In some examples, the electrode combination may include one or more anodes on one or more leads, and one or more cathodes on the same lead or a different lead, e.g., a bipolar/multipolar arrangement.

Telemetry circuitry 56 may include a RF transceiver to permit bi-directional communication between electrical stimulator 4 and programmer 40. Telemetry circuitry 56 may include an antenna 57 that may take on a variety of forms. For example, antenna 57 may be formed by a conductive coil or wire embedded in a housing associated with medical device 4. In some examples, antenna 57 may be mounted on a circuit board carrying other components of electrical stimulator 4 or take the form of a circuit trace on the circuit board. In this way, telemetry circuitry 56 may permit communication with programmer 40 in FIG. 1, to receive, for example, new programs or program groups, or adjustments to programs or program groups. Telemetry circuitry 56 may be similar to telemetry circuitry 58 of programmer 40.

Figure 4:
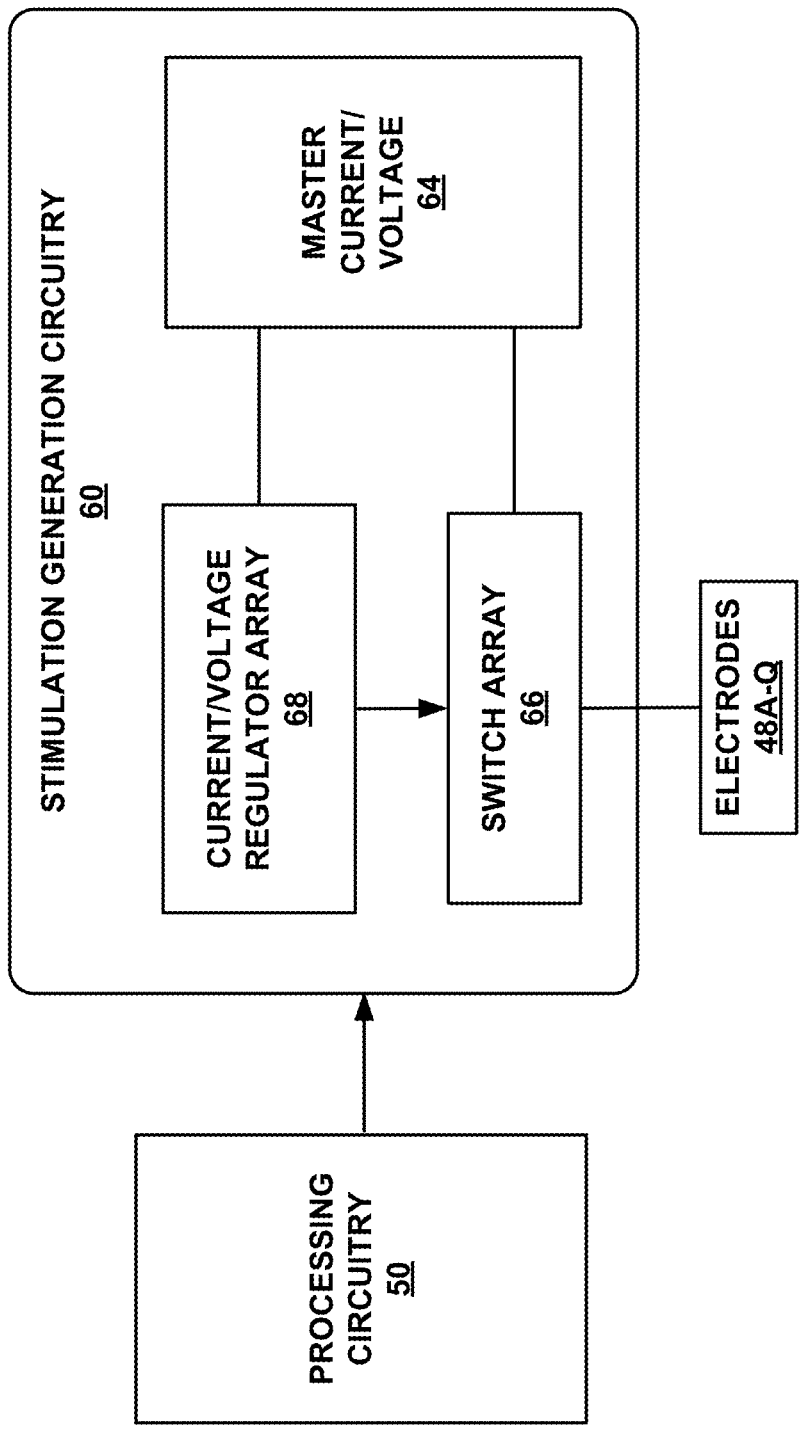
FIG. 4 is a block diagram illustrating an example of the electrical stimulation generation circuitry of the electrical stimulator of FIG. 3 in further detail.

FIG. 4 is a block diagram illustrating an example of electrical stimulation generation circuitry 60 of electrical stimulator 4 of FIG. 3 in further detail. Stimulation generation circuitry 60 may be used with an electrical stimulator, e.g., to perform the functions of stimulation generation circuitry 60 as described with reference to FIG. 3. In the example of FIG. 4, stimulation generation circuitry 60 is selectively configured to deliver current stimulation pulses to patient 6 via electrodes 48. However, this disclosure is not limited to examples in which regulated current pulses are delivered. In other examples, stimulation generation circuitry 60 may provide continuous, regulated current waveforms, rather than regulated current pulses. In some examples, stimulation generation circuitry 60 may deliver combinations of continuous waveforms and pulses, or selectively deliver either continuous waveforms or pulses. Stimulation generation circuitry 60 may generate either constant current-based or constant voltage-based stimulation in the form of pulses or continuous waveforms. Stimulation generation circuitry 60 may also be controlled to provide constant power (current-voltage product) or controlled charge stimulation pulses.

In the example illustrated in FIG. 4, stimulation generation circuitry 60 includes master current/voltage 64, and current/voltage regulator array 68. In some examples, stimulation generation circuitry 60 may further include a switch array 66. Master current/voltage 64 may provide operating power to current/voltage regulator array 68, and may include a regulated current or regulated voltage that sets the level of the master current (e.g., master electrical current amplitude) or master voltage. As shown in FIG. 4, master current/voltage 64 may be coupled to provide operating power for the current/voltage regulator array 68 and provide a master current, or master voltage when appropriate, for connection to electrodes 48. The maximum operating current level and the master current level provided to regulate current regulator array 68 may be different at any given time. For example, a master electrical current amplitude may be less than the maximum operating current level, such that the master electrical current amplitude may be increased or decreased according to minimum and maximum operating conditions. In some examples, as described with reference to FIG. 5 below, user interface 59 of external programmer 40 may display such information for a user to reference while adjusting electrical current amplitudes for various electrodes.

Processing circuitry 50 may control (e.g., via a stimulation controller) switch array 66 and current/voltage regulator array 68 to deliver stimulation via electrodes 48. In operation, processing circuitry 50 may control delivery of electrical stimulation according to one or more programs that may specify stimulation parameters such as electrode combination, electrode polarity, stimulation current amplitude, pulse rate, and/or pulse width as well as the percentage of source current distributed among or contributed by a housing anode and one or more lead anodes on one or more leads, and the percentage of sink current sunk by one or more cathodes. Programs may be defined by a user via an external controller and downloaded to an electrical stimulator 4.

Current/voltage regulator array 68 includes a plurality of regulated current sources or sinks. A current regulator may function as either a current source or sink, or be selectively configured to operate as either a source or a sink. In some examples, current/voltage regulator array 68 may regulate voltage instead of, or in addition to, current. For convenience, the term "current regulator" may be used in some instances to refer to either a source or sink. Hence, each of the current regulators in current/voltage regulator array 68 may operate as a regulated current source that delivers stimulation via a corresponding one of electrodes 48 or a regulated current sink that receives current from a corresponding one of electrodes 48, where electrodes 48 may be provided on leads, on a stimulator housing, on a leadless stimulator, or in other arrangements. Although multiple current sources or sinks are described herein, electrical stimulator 4 may include a single current source or sink in other examples and still support locking multiple electrodes into a relationship having a ratio of values for one or more therapy parameters.

Each current regulator may correspond to a plurality of current regulator branches. In some examples, the current regulator branches may be implemented in a parallel, such as with parallel current regulator branches. The number of current regulator branches defines the resolution for each current regulator. For example, the number of current regulator branches may be 64 in some examples, such that the electrical current amplitude may be adjusted for a given electrode in $1/64$ increments (i.e., a resolution of $1/64$). While 64 current branches are used for example throughout this disclosure, the techniques of this disclosure are not so limited, and the number of current branches may be more or fewer than 64 branches. For example, in some implementations, 128 current branches may be used, such that the current regulator for a particular electrode may be adjusted in $1/128$ increments (i.e., a resolution of $1/128$). In an illustrative example implementation with a resolution of $1/64$, a ring electrode at full output may implement 64 branches (e.g., $64/64^{ths}$). In addition, stimulation generation circuitry 60 may be set such that, for each of the highest contributing electrodes of the highest intensity active zone, all 64 parallel current regulator branches are used.

In examples involving leads with electrodes at different circumferential positions around the perimeter of the lead (e.g., segmented electrodes or a complex electrode array), electrodes at various axial positions of lead 12 may have a fraction maximum equal to approximately the number of branches available to the electrode divided by the number of electrodes segments in a ring of segmented electrodes. For example, ring electrodes may have a maximum of $^{64}/_{64}$ fractions in an example involving 64 current regulator branches, whereas each of N segmented electrodes in a ring of segmented electrodes may have a maximum of approximately 64/N fractions. In an illustrative example, in the case of three segmented electrodes in a ring, each electrode may have a fraction maximum of $^{21}/_{64}$ fractions. In some examples, the fraction maximum for any given electrode, including ring electrodes, may reach the full number of current regulator branches (e.g., 64 branches). That is, processing circuitry 53 or processing circuitry 50 may be configured to impose any fraction maximum based on the particular stimulation generation circuitry 60 in use (e.g., the number of current regulator branches). For example, in the case of three segmented electrodes in a ring as in the previous example, each electrode may have a fraction maximum of X/X fractions (e.g., $^{64}/_{64}$ fractions) or a fraction less than X/X that has been predefined by processing circuitry 53 or processing circuitry 50.

In examples including switch array 66, each switch of switch array 66 may couple a corresponding one of electrodes 48 to either a corresponding bi-directional current regulator of current/voltage regulator array 68 or to master current/voltage 64. In some examples, processing circuitry 50 selectively opens and closes switches in switch array 66 to configure a housing electrode (e.g., electrode(s) 48Q), and one or more of electrodes 48A-48P on one or more leads as regulated electrodes by connection to regulated current sources or sinks in current/voltage regulator array 68. In some examples, processing circuitry 50 may selectively open and close switches in switch array 66 to configure either the housing electrode, e.g., electrode 48Q, or an electrode on the lead as an unregulated electrode by connection to master current/voltage 64. In addition, processing circuitry 50 may selectively control individual regulated current sources or sinks in current/voltage regulator array 68 to deliver stimulation current pulses to the selected electrodes. In examples where switch array 66 is not used, electrodes 48 may nevertheless be coupled to current/voltage regulator array 68 and/or to master current/voltage 64.

Master current/voltage 64 may be a high or low voltage supplied by a regulated power source, depending on whether an electrode is programmed to be an unregulated source (high voltage rail) or unregulated sink (low voltage rail). Hence, master current/voltage 64 may produce high and low master current, or master voltages when appropriate, for selective coupling to unregulated, reference electrodes as needed. A regulated power source may produce one or more regulated voltage levels for use as master current/voltage 64 and for use as a power rail for current/voltage regulator array 68. Although the same master current/voltage 64 is shown as being coupled to current/voltage regulator array 68 in FIG. 4, different current amplitude may be used for the master current coupled to switch array 66 and the maximum current amplitude provided to current regulator array 68. In any event, a regulated power source may generate the regulated current amplitudes from current provided by a power source or multiple power sources, such as one or more batteries (e.g., rechargeable batteries).

Processing circuitry 50 controls the operation of switch array 66 to produce electrode configurations defined by different stimulation programs. In some cases, the switches of switch array 66 may be metal-oxide-semiconductor field-effect-transistors (MOSFETs) or other circuit components used for switching electronic signals. The switches of switch array 66 may be designed to carry an amount of unregulated current that may be coupled to a corresponding electrode through an unregulated current path associated with master current/voltage 64. In some examples, two or more regulated electrodes 48 may be intentionally programmed to deliver different amounts of current, such that the regulated electrodes produce an unbalanced current distribution. In other examples, regulated source and sink current may be balanced such that substantially all current may be sourced and sunk via respective regulated current sources and sinks.

To provide individual control of electrodes 48 as either regulated electrodes or as unregulated, reference electrodes, processing circuitry 50 controls operation of switch array 66 and current/voltage regulator array 68. When stimulation is delivered to patient 6, for the example of current pulses, processing circuitry 50 controls switch array 66 to couple selected stimulation electrodes for a desired electrode combination to respective current regulators of current/voltage regulator array 68 or to master current/voltage 64, as needed. Processing circuitry 50 controls the regulated bi-directional current sources of current/voltage regulator array 68 coupled to regulated electrodes to source or sink specified amounts of current. For example, processing circuitry 50 may control selected current sources or sinks on a pulse-by-pulse basis to deliver current pulses to corresponding electrodes.

Processing circuitry 50 also deactivates the regulated bi-directional current regulators of current/voltage regulator array 68 tied to inactive electrodes, e.g., electrodes that are not active as regulated electrodes in a given electrode configuration. Each regulated bidirectional current regulator of current/voltage regulator array 68 may include an internal enable switch controlled by processing circuitry 50 that disconnects regulated power from the current regulator or otherwise disables the current source when the corresponding electrode is not used as a regulated electrode.

The use of stimulation generation circuitry 60 as described herein enables delivery of current in fractional amounts according to a fractional use of the current regulators of current/voltage regulator array 68 and switch array 66. In this fashion, electrical stimulator 4 may deliver electrical stimulation via each of electrodes 48 that has, e.g., a fractional current amplitude of a current amplitude of each other electrode 48. Thus, the use of stimulation generation circuitry 60 allows for the adjustment of therapy parameters defining electrical stimulation therapy delivered electrodes 48 while also allowing electrical stimulator 4 to maintain a ratio of values of each therapy parameter of each of the electrodes 48 to one another.

For example, external programmer 40 of FIG. 1 defines a relationship for multiple electrodes of a plurality of electrodes 48 of electrical stimulator 4. The relationship defines a ratio of values for a therapy parameter of one or more electrodes to values of one or more other electrodes 48 used to deliver stimulation. The therapy parameter defines electrical stimulation delivered via the electrode 48 and may include, e.g., one of a current amplitude or a voltage amplitude, an electrical stimulation pulse count, a frequency, etc. External programmer 40 performs a master adjustment to adjust each value of the therapy parameters of each of the multiple electrodes 48 by an amount specified by the relationship to maintain the ratio of the values of the therapy parameters of the multiple electrodes 48. External programmer 40 controls electrical stimulator 4 to deliver electrical stimulation therapy to patient 6 in accordance with the master adjustment. Electrical stimulator 4 may use stimulation generation circuitry 60 to deliver electrical stimulation via each of electrodes 48 that has, e.g., a fractional current amplitude of a current amplitude of each other electrode 48 so as to achieve the master adjustment.

Figure 5:
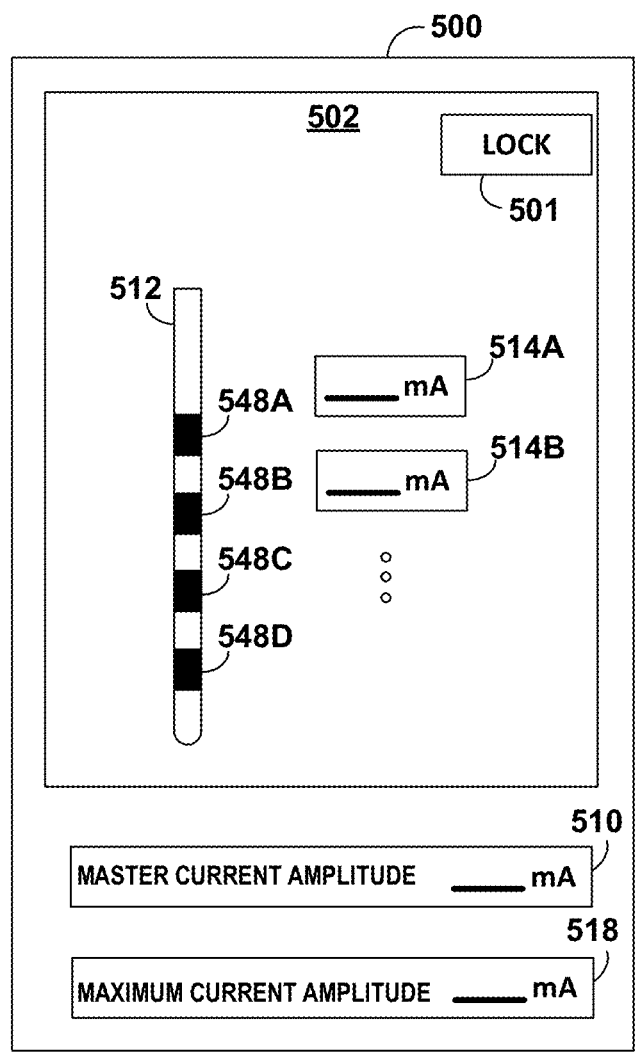
FIG. 5 is a block diagram illustrating an example user interface in accordance with the techniques of the disclosure.

FIG. 5 is a block diagram illustrating an example user interface 500 in accordance with the techniques of the disclosure. In some examples, user interface 500 is an example of user interface 59 of external programmer 40 of FIG. 2. User interface 500 may be used to adjust one or more therapy parameters of one or more electrodes 48 of one or more leads 12. Electrodes 48 are an example of electrodes 48 of FIG. 1. FIG. 5 depicts display window 502 of user interface 500, which is displaying one example lead icon 512. In some examples, user interface 500 may display a plurality of lead icons representing respective leads, each lead having one or more electrodes 48.

In the example of FIG. 5, window 502 graphically depicts an example lead icon 512 that may correspond to one of leads 12A or 12B in FIG. 1. In the illustrative example, lead icon 512 includes four electrode icons, namely electrode icons 548A-548D (referred to collectively as "electrode icons 548"). Lead icon 512 may have more, or fewer, electrode icons 548, depending on the particular lead configuration in use, and more than one lead icon 512 may be displayed on screen 502, such as icons for each of leads 12A and 12B shown in FIG. 1. For ease of illustration, only four electrode icons 548 (or a portion of four electrodes) are depicted on lead icon 512 and only two electrode icons 548A and 548B are used to illustrate the various therapy parameter adjustment examples. In addition, window 502 may depict stimulation zones, electrical field zones, activation zones, etc. (not shown). For example, a zone may be an anodal zone generated by one or more of electrodes 48 of lead 12 sourcing current. A second zone may be a cathodal zone generated by one or more of electrodes 48 of lead 12 sinking current.

In the example of FIG. 5, adjacent each of the four electrodes, display window 502 may indicate the electrical current associated with each of electrodes 48 or electrode combination. In particular, electrode icon 548A may include a fillable field or otherwise adjustable field 514A and electrode icon 548B may include another fillable field or otherwise adjustable field 514B (hereinafter, "fields 514"). Fields 514 may indicate a value of a therapy parameter of each of electrodes 48 (e.g., current amplitude in the example of FIG. 5). Although only shown with respect to electrode icons 548A and 548B (i.e., example first and second electrodes), fields 514 may apply equally to all electrodes, including segmented electrodes in the case of a segmented lead implementation.

In some examples, display window 502 of user interface 500 may include display windows 510 and 518 indicating information regarding a master therapy parameter value and/or a maximum therapy parameter value, respectively. In some examples, user interface 500 may provide an option (e.g., selectable toggle icon or menu selection) for a user to hide from display window 502 information regarding the master therapy parameter value and/or the maximum therapy parameter value. In this way, the user interface may allow the user to focus on adjusting therapy parameters for individual electrodes 48 or combinations of electrodes 48. In some examples, user interface 500 may alert the user as a desired therapy parameter value approaches a maximum value for the therapy parameter. That is, user interface 500 may hide from display windows 510 or 518 in favor of displaying the therapy parameter values for respective electrodes or electrode combinations.

In an illustrative example, user interface 500 may allow a user to provide user input directly using fields 514 to achieve a desired therapy parameter value for one or more electrodes 48. For instance, user interface 500 may accept as input '1.1' in field 514A and '1.2' in field 514B as values for a current amplitude in milliamps. In some instances, one or both fields may be prepopulated with therapy parameter values, in which case, the user may adjust the prepopulated values with adjustment values. In one example, user interface 500 may display '1.1 mA' in field 514A, indicating that an electrode corresponding to electrode icon 548A is programmed with 1.1 mA as the stimulation current amplitude. As such, user interface 500 may accept as input an adjustment to first electrode icon 548A from '1.1' to a higher or lower current amplitude value. For example, user interface 500 may accept an adjustment of first electrode icon 548A from '1.1' to '1.3'. In an example where field 514B has a prepopulated value for a therapy parameter for an electrode corresponding to electrode icon 548B, the field 514B may display a same value before and after the adjustment to first electrode icon 548A.

In some examples, a user may adjust values of therapy parameters using user interface 500, but the changes may not go into effect until a user provides an explicit command via user interface 500. For example, a user may adjust a current amplitude of electrode icon 548A from '1.1 mA' to '1.3 mA', but may desire that an electrode corresponding to electrode icon 548B stay at a current value of '1.2 mA'. Regardless of whether an explicit command is used or not, the user may adjust electrode icon 548A from '1.1 mA' to '1.3 mA' using field 514B and field 514B may display '1.2 mA' before and after the adjustment, indicating that the electrical current amplitude for an electrode corresponding to electrode icon 548B remains unchanged from '1.2 mA'. User input received via user interface 500 may be transferred from programmer 40 to electrical stimulator 4. That is electrical stimulator 4 may receive user input from programmer 40 and implement various programming requests accordingly.

In the foregoing example, fields 514A and 514B permitted the user to adjust a value of a current amplitude for electrodes corresponding to each of electrode icons 548A and 548B respectively. However, in other examples, the user may adjust one or more other therapy parameters, such as one of a voltage amplitude or a current amplitude, an electrical stimulation pulse width, an electrical stimulation pulse count, a duty cycle of the electrical stimulation, an electrical stimulation pulse rate or a frequency of the electrical stimulation, etc.

In accordance with the techniques of the disclosure, external programmer 40 receives, from the user and via user interface 500, values for current amplitudes of electrodes corresponding to electrode icon 548A and 548B via fields 514A and 514B, respectively. External programmer 40 transmits the values for the current amplitude of the electrodes to electrical stimulation 4 to control electrical stimulator 4 to deliver, via the electrodes, electrical stimulation therapy according to the respective current amplitudes of each of the electrodes.

Further, external programmer 40 can receive, from the user via a selection of lock button 501, an indication to lock a relationship for electrodes corresponding to electrode icons 548A and 548B. External programmer 40 stores an indication of the relationship between the values of the therapy parameters for each of the electrodes corresponding to electrode icons 548A and 548B. For example, external programmer 40 may determine a ratio of the value of the current amplitude specified for an electrode corresponding to electrode icon 548A to the value of the current amplitude specified for the electrode corresponding to electrode icon 548B. In some examples, by "locking" the relationship of electrode icons 548A and 548B, programmer 40 may cause electrical stimulator 4 to "lock" (e.g., maintain or preserve) the ratio of the values of the therapy parameters for each of the electrodes corresponding to electrode icons 548A and 548B to one another for later adjustments to the therapy parameters.

Subsequently, programmer 40 can receive, from the user via user interface 500, a user input requesting a master adjustment to the therapy parameters of the electrodes corresponding to electrode icons 548A and 548B. Programmer 40 responsively controls electrical stimulator 4 to adjust, based on the master adjustment, each value of the therapy parameters of each of the electrodes corresponding to electrode icons 548A and 548B by an amount specified by the relationship to maintain the ratio of the values of the therapy parameters of the electrodes corresponding to electrode icons 548A and 548B. In this fashion, programmer 40 controls electrical stimulator 4 to adjust a value of a therapy parameter of the electrical stimulation (such as, in the example of FIG. 5, a current amplitude) for, e.g., an electrode corresponding to electrode icon 548A while maintaining the relationship of the value of the therapy parameter of the electrode corresponding to electrode icon 548A to the value of the corresponding therapy parameter of an electrode corresponding to electrode icon 548B. Accordingly, a clinician may use a medical device operating in accordance with the techniques set forth herein to adjust various therapy parameters defining the electrical stimulation therapy so as to optimize therapeutic efficacy of the electrical stimulation therapy as well as reduce the occurrence and/or severity of side-effects of the electrical stimulation therapy.

Figure 6A:
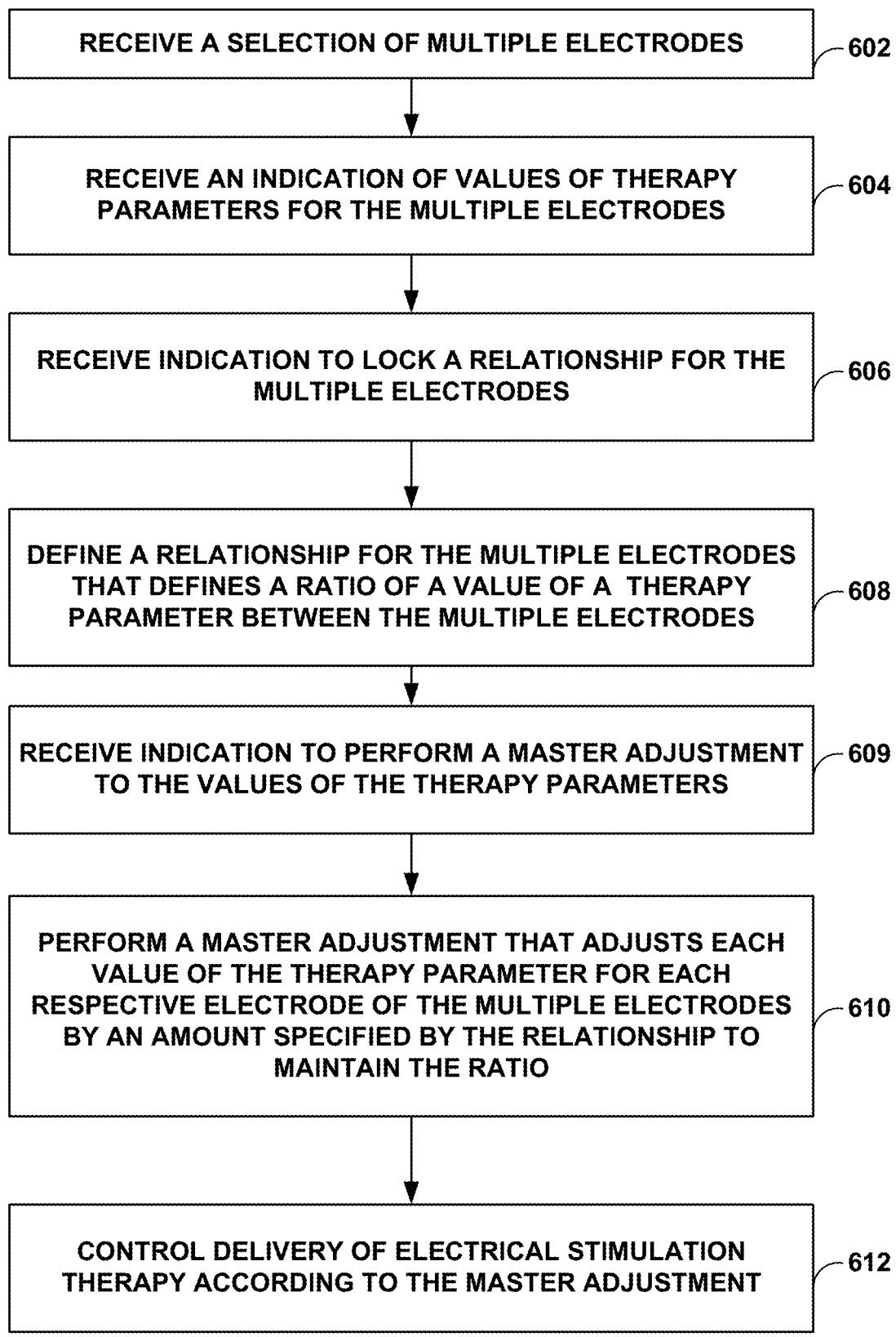
FIG. 6A is a flowchart illustrating an example operation for performing the techniques of the disclosure.

FIG. 6A is a flowchart illustrating an example operation for performing the techniques of the disclosure. Specifically, FIG. 6A illustrates an operation for locking a relationship for multiple electrodes 48. For convenience, FIG. 6A is described with respect to FIG. 1. In the example of FIG. 6A, external programmer 40 receives, from a user, a selection of multiple electrodes 48 of a plurality of electrodes 48 (602). For example, the multiple electrodes 48 may be all of the plurality of electrodes 48, or a subset of the plurality of electrodes 48. Additionally, external programmer 40 receives, from the user or from a pre-generated program, an indication of values of therapy parameters for the multiple electrodes 48 (604). Each of the values of the therapy parameters may specify, e.g., a value of one of a voltage amplitude or a current amplitude, an electrical stimulation pulse width, an electrical stimulation pulse count, a duty cycle of the electrical stimulation, an electrical stimulation pulse rate or a frequency of the electrical stimulation, etc. for each electrode 48 of the multiple electrodes 48. In some examples, external programmer 40 transmits the selection of multiple electrodes 48 and values of therapy parameters for the multiple electrodes 48 to electrical stimulator 4 to control electrical stimulator 4 to deliver electrical stimulation via the multiple electrodes 48 in accordance with the specified therapy parameters.

External programmer 40 receives, from the user, a user input requesting programmer 40 to lock a relationship for the multiple electrodes (606), and in response, programmer 40 defines a relationship for the multiple electrodes that defines a ratio of a value of a therapy parameter between the multiple electrodes (608). In some examples, external programmer 40 stores an indication of the relationship between the values of the therapy parameters for each of the multiple electrodes 48. As an example, external programmer 40 may determine a ratio of a value of a current amplitude specified for, e.g., electrode 48A to a value of a current amplitude specified for, e.g., electrode 48B.

Subsequently, external programmer 40 receives, from the user, an indication to perform a master adjustment to the values of the therapy parameters (609). In response to receiving the indication, external programmer performs the master adjustment to adjust each value of the therapy parameters for each respective electrode of the multiple electrodes by an amount specified by the relationship to maintain the ratio (610). External programmer 40 then transmits the adjusted values of the therapy parameters for the multiple electrodes 48 to electrical stimulator 4 to control delivery of electrical stimulation by electrical stimulator 4 in accordance with the master adjustment (612).

Figure 6B:
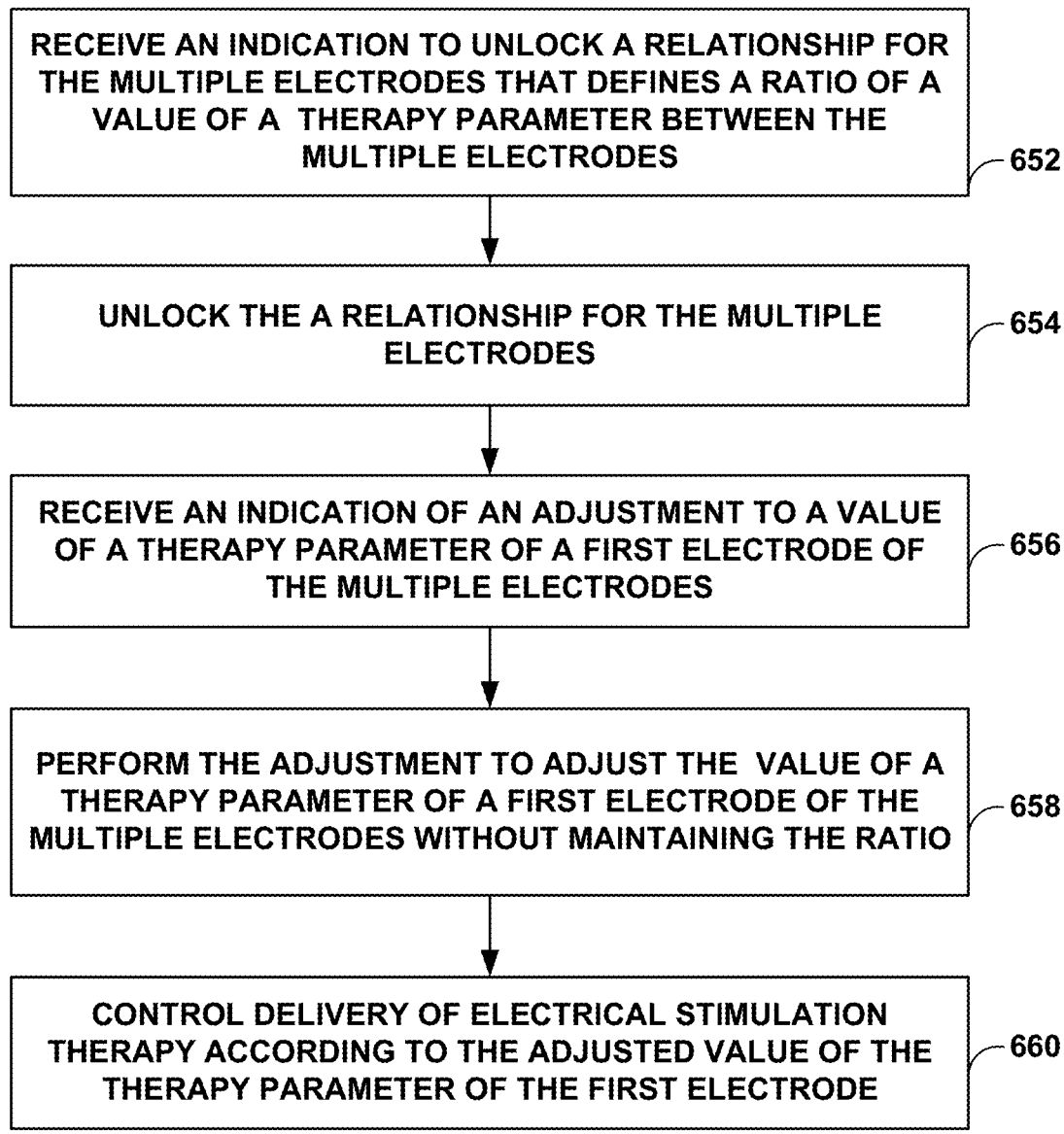
FIG. 6B is a flowchart illustrating an example operation for performing the techniques of the disclosure.

FIG. 6B is a flowchart illustrating an example operation for performing the techniques of the disclosure. Specifically, FIG. 6B illustrates an operation for unlocking a relationship for multiple electrodes 48. For convenience, FIG. 6B is described with respect to FIG. 1. In some examples, the operation of FIG. 6B may occur after the operation described above with respect to FIG. 6A. In the example of FIG. 6B, external programmer 40 receives, from a user, an indication to unlock a relationship for multiple electrodes 48 of a plurality of electrodes 48 (652). The relationship for the multiple electrodes defines a ratio of a value of a therapy parameter between the multiple electrodes. Each of the values of the therapy parameters may specify, e.g., a value of one of a voltage amplitude or a current amplitude, an electrical stimulation pulse width, an electrical stimulation pulse count, a duty cycle of the electrical stimulation, an electrical stimulation pulse rate or a frequency of the electrical stimulation, etc. for each electrode 48 of the multiple electrodes 48. In some examples, the multiple electrodes 48 may be all of the plurality of electrodes 48, or a subset of the plurality of electrodes 48.

In some examples, the user may specify the indication to unlock a relationship by selecting an icon displayed by user interface 59 of programmer 40 that corresponds to a particular one of the locked multiple electrodes 48. In some examples, the user may specify the indication to unlock a relationship by changing, via the user interface 59 of programmer 40, an amplitude of one or more specific electrodes 48. In response to receiving the indication to unlock the relationship, external programmer 40 unlocks the relationship for the multiple electrodes 48 (654). For example, external programmer 40 may clear any previous relationship between electrodes 48 and no relationship between electrodes 48 is defined.

After clearing the relationship, external programmer 40 receives an indication of an adjustment to a value of a therapy parameter of a first electrode of the multiple electrodes 48 (656). External programmer 40 performs the adjustment to adjust the value of the therapy parameter of the first electrode of the multiple electrodes 48 without maintaining the ratio of the value of the therapy parameter between the multiple electrodes 48 specified by the previous relationship (658). External programmer 40 then transmits the adjusted value of the therapy parameter of the first electrode of the multiple electrodes 48 to electrical stimulator 4 to control delivery of electrical stimulation by electrical stimulator 4 in accordance with the adjusted value of the therapy parameter of the first electrode (660).

Figure 7A:
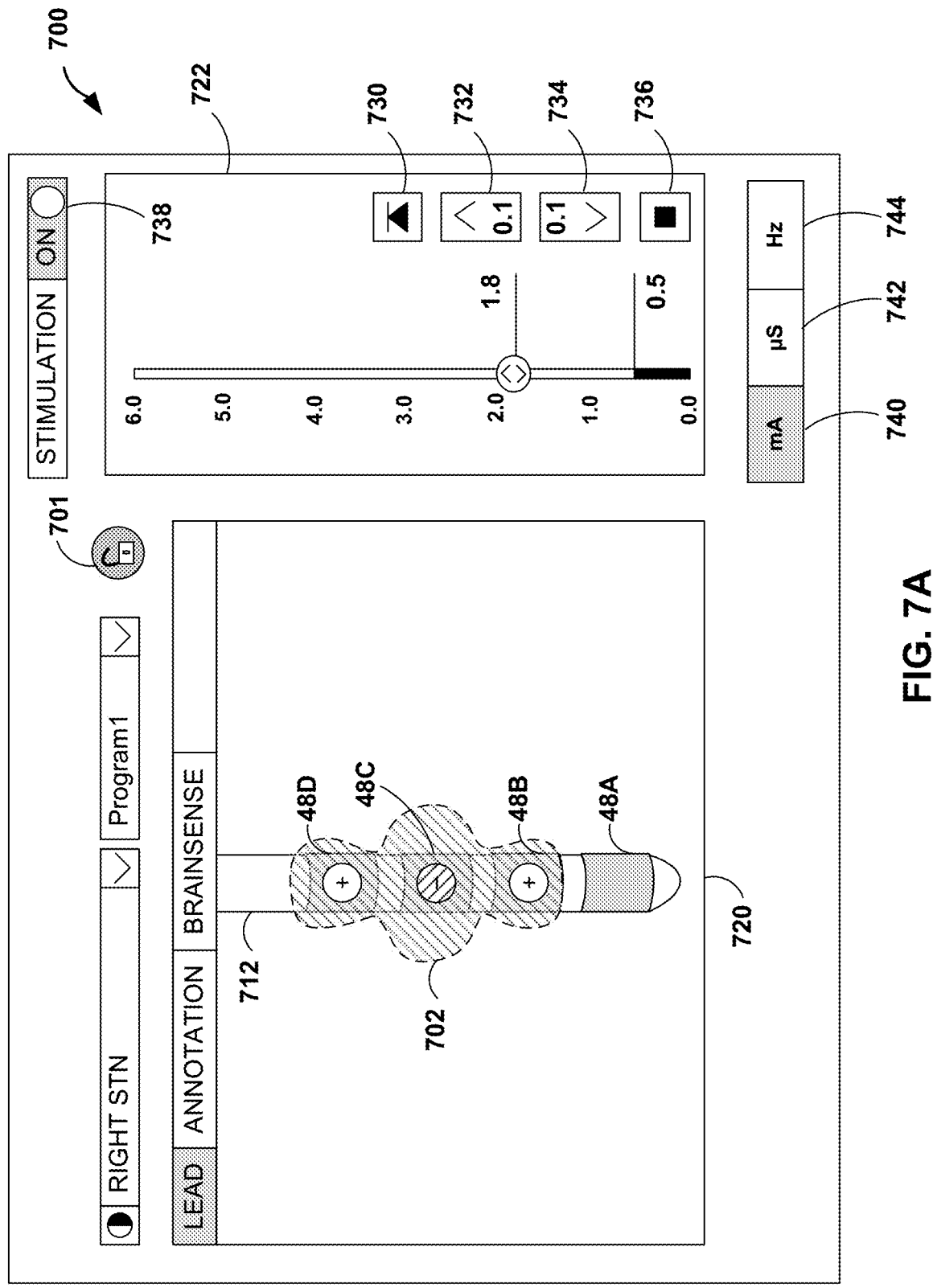
FIGS. 7A-7B are conceptual diagrams illustrating screens of an example user interface in accordance with the techniques of the disclosure.
Figure 7B:
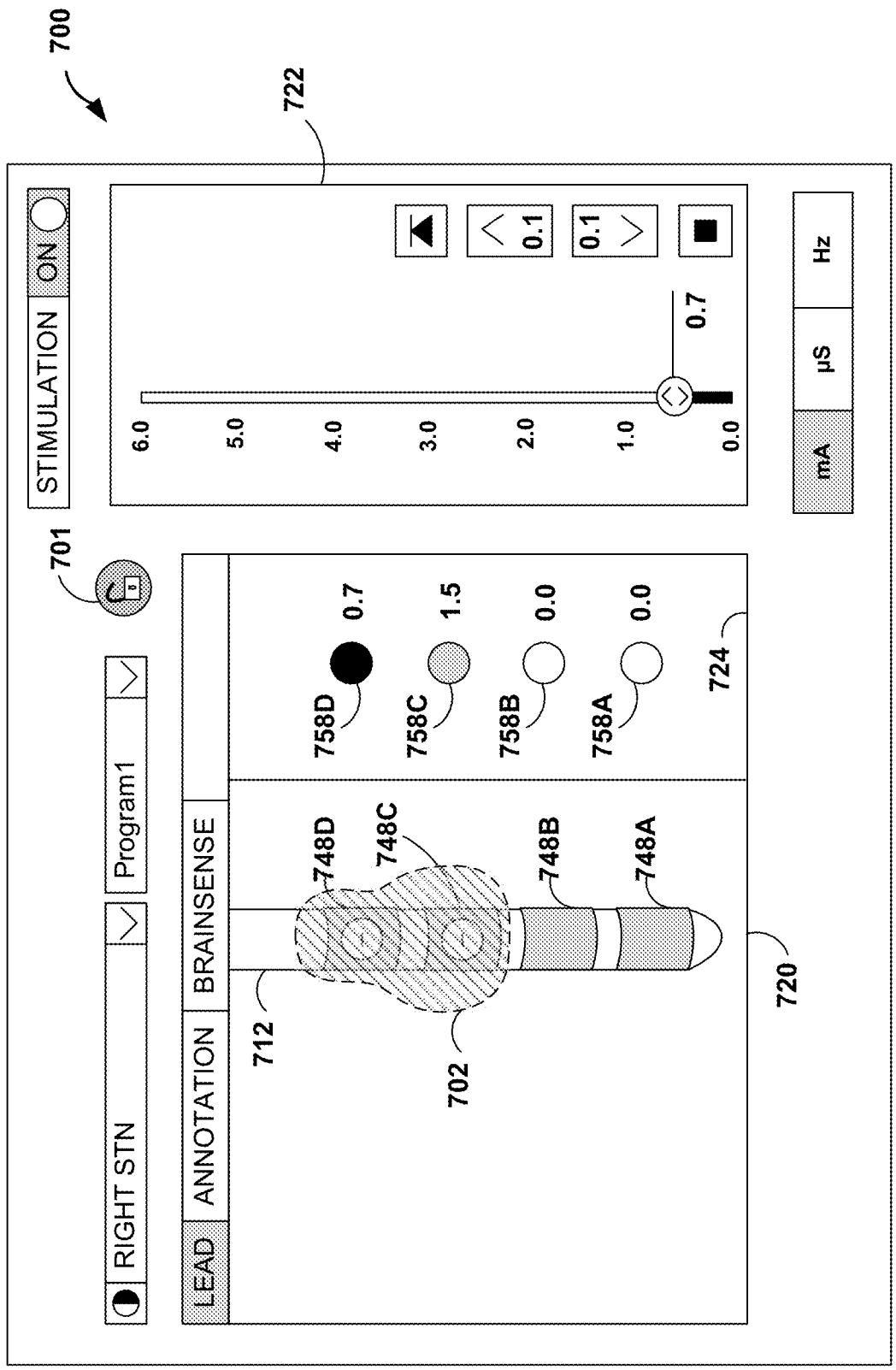

FIGS. 7A-7B are conceptual diagrams illustrating screens of an example user interface 700 in accordance with the techniques of the disclosure. User interface 700 may be an example of user interface 59 of programmer 40 of FIG. 2 or user interface 50 of FIG. 5.

User interface 700 depicts a representation of electrode icons 748A-48D (hereinafter, "electrode icons 748") disposed on lead icon 712 within display window 720. In the example of FIGS. 7A-7B, each of electrode icons 748A-748D correspond to a respective one of electrodes 48A-48D of FIGS. 1 and 3, and lead icon 712 corresponds to lead 12 of FIG. 1. In the example of FIG. 7A, electrode icons 748D and 748B indicate that electrodes 48D and 48B are selected to act as cathodes and electrode icon 748C indicates that electrode 48C is selected to act as an anode. Display window 720 further depicts a representation of an electrical field 702 generated by delivery of electrical stimulation by electrical stimulator 4 according to therapy parameters selected for electrodes 48B, 48C, and 48D.

User interface 700 includes a toggle button 738 that allows a clinician to activate or deactivate delivery of electrical stimulation by electrical stimulator 4 according to therapy parameters selected for electrodes 48B, 48C, and 48D. User interface 700 further includes therapy parameter control panel 722 that allows a clinician to adjust values of therapy parameters for a currently-selected electrode 48. In the example of FIG. 7A, the clinician has selected electrode icon 748C and set a value of 1.8 milliamps for a current amplitude of electrical stimulation delivered via electrode 48C. The user may adjust the value of the therapy parameter for electrode 48C by pressing incremental increase button 732 or incremental decrease button 734. In this example, incremental increase button 732 and incremental decrease button 734 adjust the value of the therapy parameter by 0.1 milliamps. Further, the clinician may adjust the value of the therapy parameter for electrode 48C to a maximum value by pressing maximum button 730 or a minimum value by pressing minimum button 736. The maximum or minimum values may be predetermined based on patient comfort and stimulation efficacy or predetermined based on system limits. Alternatively or in addition, the user may proportionally adjust the stimulation field of the entire active electrode level using the amplitude slider. The clinician may select the type of therapy parameter (e.g., current amplitude, pulse duration, or pulse frequency) by selecting a corresponding therapy parameter type button such as milliamp button 740, pulse duration button 742, or pulse frequency button 744.

In the example of FIG. 7B, electrode icons 748D and 748C indicate that electrodes 48D and electrode 48C are selected to act as anodes. Electrode 48B may act as a cathode and/or a remote electrode on the stimulator 4 may be acting as an electrode, for example. As depicted in FIG. 7B, user interface 700 further includes electrode selection panel 724. Electrode selection panel 724 includes indicators 758A-758D (collectively, "indicators 758") that each depict a selection status for a corresponding one of electrodes 48A-48D. As depicted in FIG. 7B, indicator 758D (shaded in black) denotes that the clinician has selected electrode 48D for therapy parameter adjustment (e.g., via therapy parameter control panel 722). As depicted in electrode selection panel 724, the clinician has set a value of 0.7 milliamps for a current amplitude of electrical stimulation delivered via electrode 48D. Indicator 758C (shaded in gray) denotes that the clinician has selected electrode 48C for delivery of stimulation but is not currently adjusting the therapy parameters of electrode 48C. As depicted in electrode selection panel 724, the clinician has previously set a value of 1.5 milliamps for a current amplitude of electrical stimulation delivered via electrode 48C. Indicators 758A and 758B (shaded in white) denote that electrodes 48A and 48B are not used for delivery of stimulation. As depicted in electrode selection panel 724, a value of 0.0 milliamps is set for a current amplitude of electrical stimulation delivered via electrodes 48A and 48B.

The status color of indicators 758 (e.g., black, gray, or white) indicates the current status of therapy delivery by electrical stimulator 4 using respective electrodes 48. For example, as discussed above, the color black in FIG. 7B indicates an electrode that is currently selected for therapy parameter adjustment via therapy parameter control panel 722. As another example, the color gray in FIG. 7B indicates an electrode that has a therapy parameter greater than zero (e.g., such that the electrode is actively used for delivery of electrical stimulation therapy) but is not currently being adjusted via therapy parameter control panel 722. As another example, the color white in FIG. 7B indicates an electrode that has a therapy parameter equal than zero (e.g., such that the electrode is not used for delivery of electrical stimulation therapy) and is not currently being adjusted via therapy parameter control panel 722. In examples where user interface 700 is a touch-sensitive display, a clinician may select a particular electrode 48 for adjustment via therapy parameter control panel 722 by pressing an indicator 758 that corresponds to the desired electrode 48. Further, therapy parameter control panel 722 may automatically update to display values of the therapy parameter for electrodes 48 that correspond to the currently-selected electrode icon 758. The colors of FIG. 7B are provided for ease of illustration only, and other colors may be used to indicate various statuses or configurations of electrodes 48.

In accordance with the techniques of the disclosure, user display 700 of FIGS. 7A-7B further includes lock button 701. User interface 700 may operate in an "unlocked" or "locked" configuration when allowing the user to define values of therapy parameters for delivery of electrical stimulation by electrical stimulator 4. The user may toggle between the "unlocked" and "locked" configurations by selecting lock button 701. Lock button 701 may allow the user to "lock" a shape of electrical field 702, as described in further detail below. In some examples, lock button 701 includes three elements: a button, an icon, and an amplitude value. Lock button 701 allows the user to scale the whole shape of stimulation field 702 up or down by maintaining the ratio of parameter values amongst the locked electrodes.

In the "unlocked" configuration of user interface 700, no relationship between any of electrodes 48 is defined. The user may adjust values of individual therapy parameters of each of electrodes 48. In some examples, the user adjusts values of individual therapy parameters of each of electrodes 48 to achieve a desired shape of electrical field 702 created by delivery of electrical stimulation by stimulator 4 in accordance with the selected therapy parameters. In the "unlocked" configuration, the value on the amplitude stimulation slider of therapy parameter control panel 722 shows an amplitude of a single selected electrode (e.g., the electrode corresponding to electrode icon 758D).

In the "locked" configuration of user interface 700, programmer 40 defines a relationship for the selected electrodes 48 (e.g., electrodes 48 corresponding to electrode icons 758D and 758C in FIG. 7B). The relationship defines a ratio of a value of a therapy parameter between the multiple electrodes. While in the "locked" configuration, the user may request external programmer 40 to perform a master adjustment. The master adjustment adjusts each value of the therapy parameter for each respective electrode of the selected electrodes 48 by an amount specified by the relationship so as to maintain the ratio of the value of the therapy parameter between the multiple selected electrodes 48. In the "locked" configuration, the value on the amplitude stimulation slider of therapy parameter control panel 722 shows the master amplitude.

After performing the master adjustment, the user again select lock button 701 to transition user interface 700 back to the "unlocked" configuration. While in the "unlocked" configuration, any previous relationship between electrodes 48 is cleared and no relationship between electrodes 48 is defined. In some examples, user interface 800 may transition to the "unlocked" configuration by selecting a single electrode icon 758 or by selecting lock button 701. The user may again adjust values of individual therapy parameters of each of electrodes 48 without maintaining the previously-defined relationship. In this manner, user interface 700 may be configured to enable a user to quickly increase or decrease a stimulation field while maintaining the field shape. Then, the user can unlock the relationship and adjust single electrodes and make smaller adjustments to the stimulation field as desired. Alternatively or in addition, the user may select lock button 701 again to transition user interface 700 a second time to the "locked" configuration to perform another master adjustment, etc.

Figure 8A:
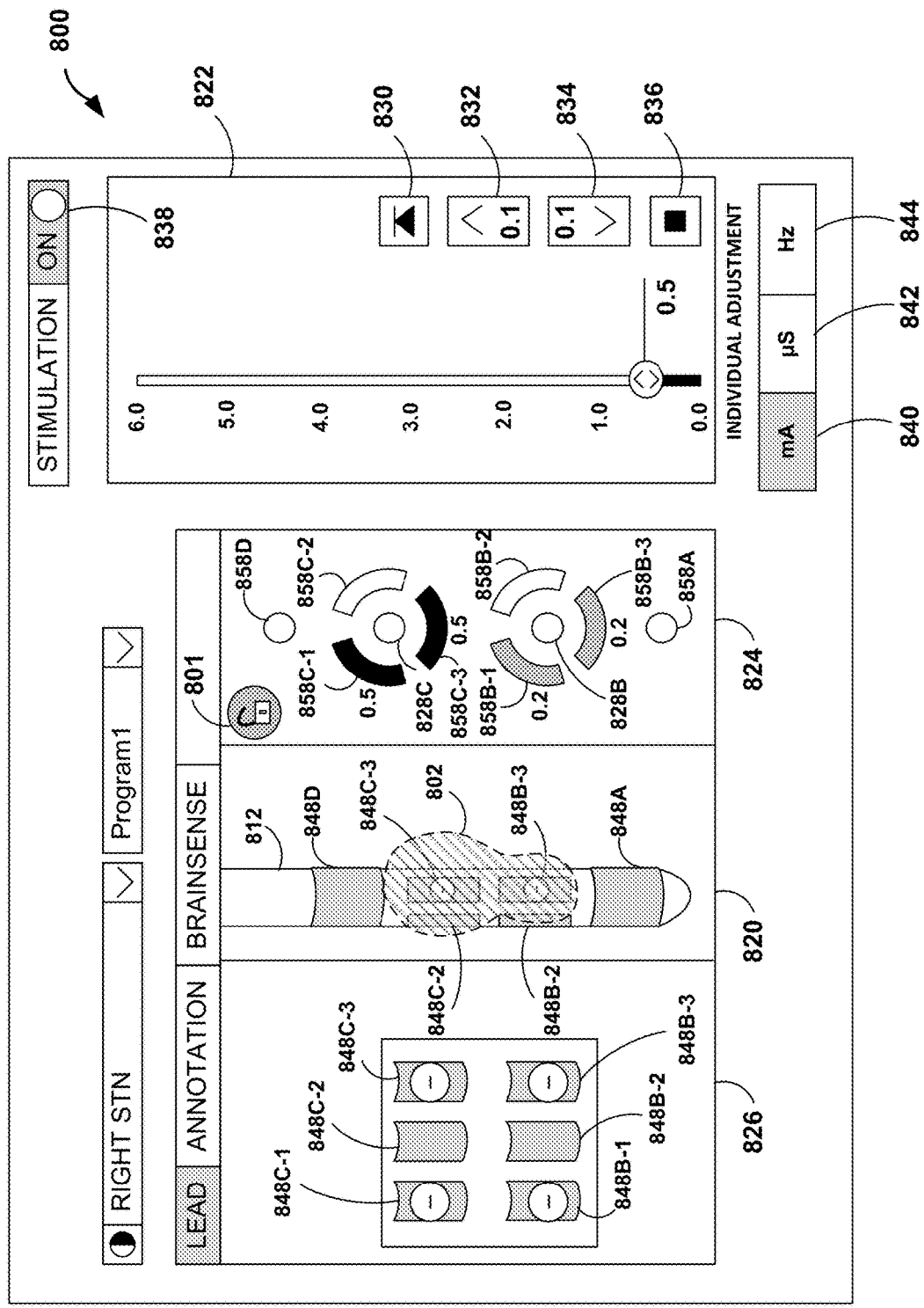
FIGS. 8A-8B are conceptual diagrams illustrating screens of an example user interface in accordance with the techniques of the disclosure.
Figure 8B:
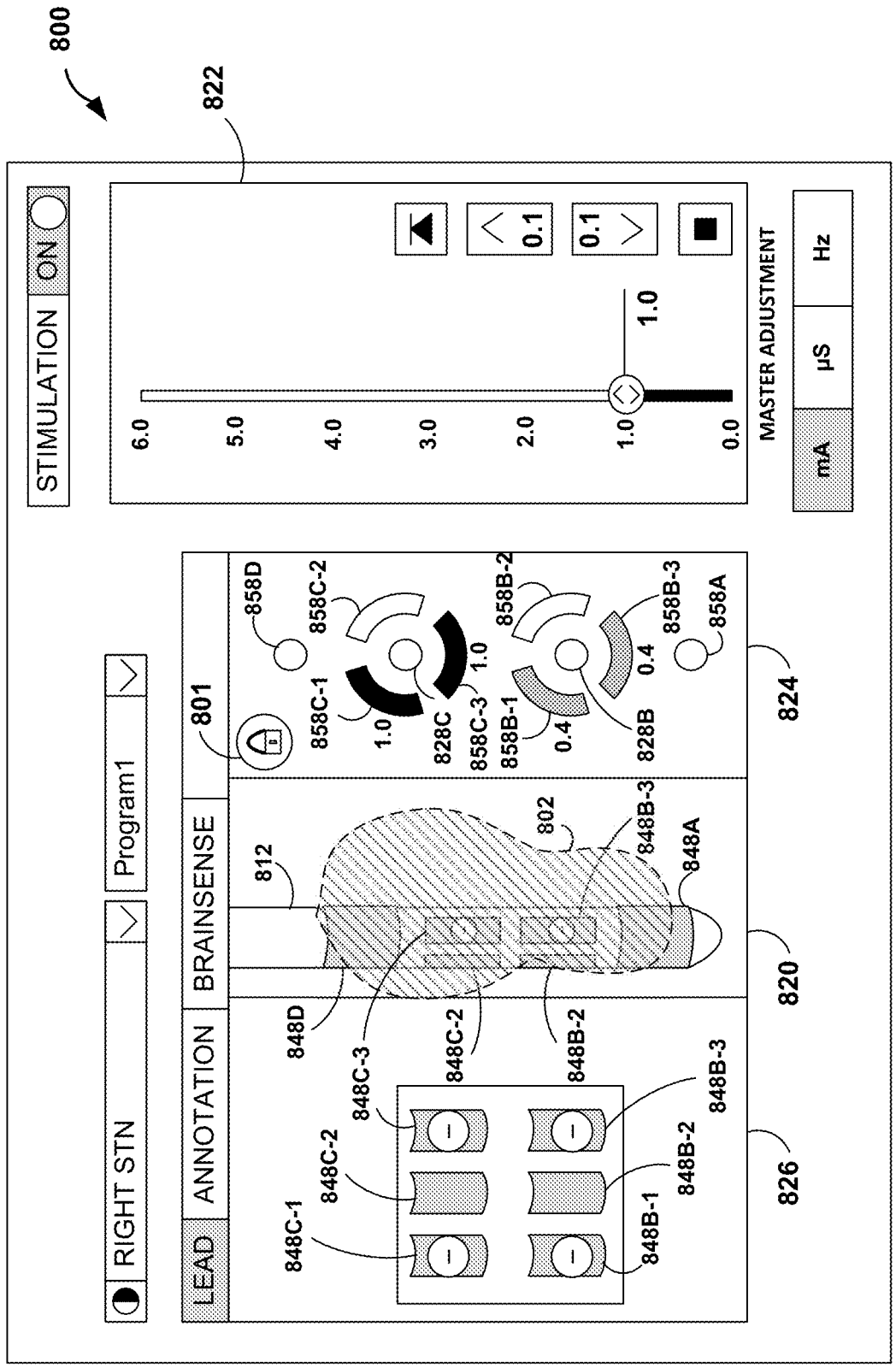

FIGS. 8A-8B are block diagrams illustrating an example user interface in accordance with the techniques of the disclosure. User interface 800 may be an example of user interface 59 of programmer 40 of FIG. 2 or user interface 50 of FIG. 5.

As depicted in FIG. 8A, user interface 800 depicts a representation of electrode icons 848A, 848B-1, 848B-2, 848B-3, 848C-1, 848C-2, 848C-3, and 848D (hereinafter, "electrode icons 848") disposed on lead 812 within display window 820.

In the example of FIGS. 8A-8B, each of electrode icons 848A-848D correspond to a respective one of electrodes 48 of FIGS. 1 and 3, and lead icon 812 corresponds to lead 12 of FIG. 1.

In the example of FIG. 8A, electrode icons 848B-1, 848B-2, 848B-3 (collectively, "electrode icons 848B") represent a first subset of electrodes 48 disposed at different circumferential positions around lead 12. Similarly, electrode icons 848C-1, 848C-2, 848C-3 (collectively, "electrode icons 48C") represent a second subset of electrodes 48 disposed at different circumferential positions around lead 12. While in the example of FIG. 8A, each of the first subset of electrodes 48 and second subset of electrodes 48 are represented by three electrode icons (e.g., electrode icons 848B-1, 848B-2, 848B-3 in the first subset and electrode icons 848C-1, 848C-2, 848C-3 in the second subset), in other examples each subset of electrodes 48 may have any number of electrodes (e.g., more than or fewer than 3 electrodes per subset). Furthermore, while in the example of FIG. 8A, lead icon 812 has two rings of subsets of electrode icons 848, in other examples lead icon 812 may have more rings, fewer rings, or no rings of electrode icons 848, each ring including a subset of one or more electrodes 848, dependent on the actual configuration of lead 12.

In the example of FIG. 8A, electrode icons 848B-1, 848B-2, 848C-1, and 848C-2 indicate that corresponding electrodes 48 are selected to act as anodes for delivery of electrical stimulation by electrical stimulator 4 of FIG. 1. One or more of ring electrodes 48D, 48A, or a housing of a medical device, such as electrical stimulator 4 of FIG. 1 (not depicted in FIG. 8A), may act as cathodes in this example. Display window 820 further depicts a representation of an electrical field 802 generated by delivery of electrical stimulation by electrical stimulator 4 according to therapy parameters selected for electrodes corresponding to electrode icons 848B-1, 848B-2, 848C-1, and 848C-2.

User interface 800 includes a toggle button 838 that allows a clinician to activate or deactivate delivery of electrical stimulation by electrical stimulator 4 according to therapy parameters selected for electrodes corresponding to 848B-1, 848B-2, 848C-1, and 848C-2. Toggle button 838 may operate in a substantially similar fashion to toggle button 738 of FIG. 7A.

User interface 800 further includes electrode status window 826, which displays a side view of the status of electrodes 48. For example, as depicted in the example of FIG. 8A, electrode status window 826 depicts electrode icons 848B-1, 848B-2, 848C-1, and 848C-2 indicating corresponding electrodes 48 as acting as anodes for delivery of electrical stimulation by electrical stimulator 4. For implementations where lead 12 includes a subset of electrodes 48 disposed on a ring around lead 12, such as the case for, e.g., electrodes corresponding to electrode icons 848B-1, 848B-2, and 848B-3, the use of electrode status window 826 may assist the clinician in viewing a status of each of electrodes 48 where one or more of the electrode icons 848 may be obscured from view by the 3-dimensional depiction of lead icon 812 within display window 820. For example, as depicted in the example of FIG. 8A, electrode icons 848B-1 and 848C-1 are at least partially obscured by the 3-dimensional depiction of lead icon 812 within display window 820.

User interface 800 further includes electrode selection panel 824. As depicted in FIG. 8A, electrode selection panel 824 includes indicators 858A, 858B-1, 858B-2, 858B-3, 858C-1, 858C-2, 858C-3, and 858D that each depict a selection status for a corresponding axial representation (e.g., a cross-sectional view of the different axial positions corresponding to electrode locations) of one of electrode icons 848A, 848B-1, 848B-2, 848B-3, 848C-1, 848C-2, 848C-3, and 848D. As depicted in FIG. 8A, indicators 858C-1 and 858C-3 (shaded in black) denote that the clinician has selected electrodes corresponding to electrode icons 848C-1 and 848C-3 for therapy parameter adjustment (e.g., via therapy parameter control panel 822). As depicted in electrode selection panel 824, the clinician has set a value of 0.5 milliamps for a current amplitude of electrical stimulation delivered via each of electrodes corresponding to electrode icons 848C-1 and 848C-3. Indicators 858B-1 and 858B-3 (shaded in gray) denote that the clinician has selected electrodes 48 corresponding to electrode icons 848B-1 and 848B-3 for delivery of stimulation but is not currently adjusting the therapy parameters of such electrodes. As depicted in electrode selection panel 824, the clinician has previously set a value of 0.2 milliamps for a current amplitude of electrical stimulation delivered via each of electrodes 48 corresponding to electrode icons 848B-1 and 848B-3. Indicators 858A, 858B-2, 858C-2, and 858B (shaded in white) denote that electrodes 48 corresponding to electrode icons 848A, 848B-2, 848C-2, and 848D are not currently used for delivery of stimulation.

In some examples, when active, indicators 858 display a value of an amplitude and a label in both the interactive and selected state. Indicators 858 controls are single-select options, e.g., tapping a second button switches from the first to the second. Each indicator 858 displays an amplitude of a corresponding single electrode 48. In some examples, display window 820 displays a total amplitude for each ring or an amplitude for each electrode within each ring.

Electrode selection panel 824 further includes ring toggle buttons 828B and 828C. Ring toggle buttons 828B and 828C allow a clinician to toggle on or off all of the electrodes of a ring with one button. For example, a clinician may select ring toggle button 828B to transition each of electrodes 48 corresponding to electrode icons 848B-1, 848B-2, and 848B-3 to an "on" state. In some examples, when selecting ring toggle button 828B, each of electrodes corresponding to electrode icons 848B-1, 848B-2, and 848B-3 that were previously in an "off" state may transition to an "on" state and use a predefined value for a therapy parameter (e.g., an initial current amplitude) for delivery of electrical stimulation. Furthermore, a clinician may select ring toggle button 828B a second time to transition each of electrodes corresponding to electrode icons 848B-1, 848B-2, and 848B-3 to an "off" state.

In some examples, each ring toggle button 828B, 828C selects only the available electrodes on the same ring that are active. For example, if only two segments 858C-1 and 858C3 are part of the configuration, ring toggle button 828C only selects 858C-1 and 858C3 and not 858C-2.

User interface 800 further includes therapy parameter control panel 822 that allows a clinician to adjust values of therapy parameters for one or more currently-selected electrodes 48. In the example of FIG. 8A, the clinician has selected electrodes 48 corresponding to electrode icons 848C-1 and 848C-3 and set a value of 0.5 milliamps for a current amplitude of electrical stimulation delivered via the electrodes. Therapy parameter control panel 822 may operate in a substantially similar fashion as therapy parameter control panel 722 of FIGS. 7A-7B. For example, the user may adjust the value of the therapy parameter for electrodes 48 corresponding to electrode icons 848C-1 and 848C-3 by pressing incremental increase button 832, incremental decrease button 834, maximum button 830, or minimum button 836, each of which may operate in a substantially similar fashion to like buttons 732, 734, 730, or 736 of FIG. 7A. Furthermore, the clinician may select the type of therapy parameter (e.g., current amplitude, pulse duration, or pulse frequency) by selecting a corresponding therapy parameter type button such as milliamp button 840, pulse duration button 842, or pulse frequency button 844.

The status color of indicators 858 (e.g., black, gray, or white) indicates the current status of therapy delivery by electrical stimulator 4 using respective electrodes 48. The status color of indicators 858 may operate in a substantially similar fashion as the status color of indicators 758 discussed above with respect to FIG. 7A. As an example, where user interface 700 is a touch-sensitive display, a clinician may select a particular electrode 48 for adjustment via therapy parameter control panel 822 by pressing an indicator 858 that corresponds to the desired electrode 48. Further, therapy parameter control panel 822 may automatically update to display values of the therapy parameter for the currently-selected electrode 48. The colors of FIG. 8A are provided for ease of illustration only, and other colors may be used to indicate various statuses or configurations of electrodes 48.

Electrode selection panel 824 includes lock button 801. User interface 800 may operate in an "unlocked" or "locked" configuration when allowing the user to define values of therapy parameters for delivery of electrical stimulation by electrical stimulator 4. The user may toggle between the "unlocked" and "locked" configurations by selecting lock button 801. Lock button 801 may allow the user to "lock" a shape of electrical field 802, as described in further detail below. In some examples, lock button 801 includes three elements: a button, an icon, and an amplitude value. Lock button 801 allows the user to scale the whole shape of stimulation field 802 up or down by maintaining the ratio of parameter values amongst the locked electrodes.

In the example of FIG. 8A, user interface 800 is in the "unlocked" configuration. While in the "unlocked" configuration, no relationship between any of electrodes 48 is defined. The user may adjust values of individual therapy parameters of each of electrodes 48. In some examples, the user adjusts values of individual therapy parameters of each of electrodes 48 to achieve a desired shape of electrical field 802 created by delivery of electrical stimulation by stimulator 4 in accordance with the selected therapy parameters.

In response to a user selecting lock button 801, user interface 800 transitions into the "locked" configuration. During this transition to the "locked" configuration, external programmer 40 defines a relationship between each of electrodes 48. In some examples, the relationship defines a ratio of a value of a therapy parameter of each of electrodes 48 to values of corresponding therapy parameters of each of the other electrodes 48. For example, as depicted in the example of FIG. 8A, electrodes 48 corresponding to electrode icons 858B-1 and 858B-3 have a value for a current amplitude of 0.2 milliamps, and electrodes 858C-1 and 858C-3 have a value for a current amplitude of 0.5 milliamps. With reference to electrode icon 858B-1, there is a 1:1 ratio of the current amplitude of the electrode corresponding to electrode icon 858B-1 to the electrode corresponding to electrode icon 858B-3 (e.g., 0.2:0.2 milliamps) and a 1:2.5 ratio of the current amplitude of the electrode corresponding to electrode icon 858B-1 to each of the electrodes corresponding to electrode icons 858C-1 and 858C-3 (e.g., 0.2: 0.5 milliamps). External programmer 40 may store the ratios for each of the electrodes so that external programmer 40 may maintain the ratios when performing a master adjustment to the therapy parameters while user interface 800 is in the "locked" configuration, as described in additional detail below with respect to FIG. 8B.

User interface 800 of FIG. 8B may operate in a substantially similar fashion as user interface 800 of FIG. 8A. However, user interface 800 has transitioned into the "locked" configuration in response to the user selecting lock button 801, as discussed above with respect to FIG. 8A. In some examples, when lock button 801 is turned on, all of the cathodes in the electrode configuration are visually selected and continue to be selected until the master amplitude is turned off. The value on the amplitude stimulation slider of therapy parameter control panel 822 shows the master amplitude.

As depicted in the example of FIG. 8B, the user requests, via therapy parameter control panel 822, that programmer 40 performs a master adjustment to adjust each value of the therapy parameters of each of the selected electrodes 48 (e.g., electrodes corresponding to electrode icons 858B-1, 858B-3, 858C-1, and 858C-3) while maintaining the locked relationship values. In the example of FIG. 8, the user has selected electrodes 48 corresponding to 858C-1 and 858C-3. Previously, a value of 0.5 milliamps had been set for a current amplitude of electrical stimulation delivered via each of electrodes 48 corresponding to 858C-1 and 858C-3 and has performed a master adjustment to adjust the value of the current amplitude of electrical stimulation delivered via each of electrodes 48 corresponding to 858C-1 and 858C-3 to 1.0 milliamps.

Furthermore, because user interface 800 is in the "locked" configuration, external programmer 40 adjusts each value of the therapy parameters of each of the other selected electrodes 48 (e.g., electrodes corresponding to electrode icons 858B-1 and 858B-3) by an amount specified by the relationship so as to maintain the ratios of the therapy parameters between each of electrodes 858B-1, 858B-3, 858C-1, and 858C-3 when performing the master adjustment. For example, as discussed above, with reference to the electrode corresponding to electrode icon 858B-1, external programmer 40 has stored a 1:1 ratio of the current amplitude of the electrode corresponding to electrode icon 858B-1 to the electrode corresponding to electrode icon 858B-3 (e.g., 0.2:0.2 milliamps) and a 1:2.5 ratio of the current amplitude of the electrode corresponding to electrode icon 858B-1 to each of the electrodes corresponding to electrode icons 858C-1 and 858C-3 (e.g., 0.2:0.5 milliamps). Therefore, when performing the master adjustment to adjust the value of the current amplitude of electrical stimulation delivered via each of the electrodes corresponding to electrode icons 858C-1 and 858C-3 from 0.5 milliamps to 1.0 milliamps, external programmer 40 further adjusts the value of the current amplitude of electrical stimulation delivered via each of the electrodes corresponding to electrode icons 858C-1 and 858C-3 from 0.2 milliamps to 0.4 milliamps to maintain the ratios of the therapy parameters of each of the electrodes corresponding to electrode icons 858B-1, 858B-3, 858C-1, and 858C-3 to one another.

Accordingly, upon performing the master adjustment, the electrodes corresponding to electrode icons 858B-1 and the electrodes corresponding to electrode icons 858B-3 have a value of a current amplitude of 0.4 milliamps and the electrodes corresponding to electrode icons 858C-1 and 858C-3 have a value of a current amplitude of 1.0 milliamps. Therefore, after performing the master adjustment, there is a 1:1 ratio of the current amplitude of the electrode corresponding to electrode icon 858B-1 to the electrode corresponding to electrode icon 858B-3 (e.g., 0.4:0.4 milliamps) and a 1:2.5 ratio of the current amplitude of the electrode corresponding to electrode icon 858B-1 to each of the electrodes corresponding to electrode icons 858C-1 and 858C-3 (e.g., 0.4:1.0 milliamps). Furthermore, as depicted in the example of FIG. 8B, upon performing the master adjustment, the size (e.g., the volume of tissue activation) of electrical field 802 has increased, while the overall shape of electrical field 802 is substantially the same as the shape of electrical field 802 prior to performing the master adjustment (e.g., electrical field 802 of FIG. 8A). External programmer 40 may thereafter control electrical stimulator 4 to deliver electrical stimulation to patient 6 in accordance with the adjusted therapy parameters and via electrodes 48 corresponding to selected electrode icons 858B-1, 858B-3, 858C-1, and 858C-3.

After performing the master adjustment, the user may again select lock button 801 to transition user interface 800 back to the "unlocked" configuration. While in the "unlocked" configuration, any previous relationship between electrodes 48 is cleared and no relationship between electrodes 48 is defined. In some examples, user interface 800 may transition to the "unlocked" configuration by selecting a single electrode icon 848 or 858 or by turning off lock button 801. The user may again adjust values of individual therapy parameters of each of electrodes 48 without maintaining the previously-defined relationship. In this manner, user interface 800 may be configured to enable a user to quickly increase or decrease a stimulation field while maintaining the field shape. Then, the user can unlock the relationship and make adjustments to single electrodes and make smaller adjustments to the stimulation field as desired. Alternatively or in addition, the user may select lock button 801 again to transition user interface 800 a second time to the "locked" configuration to perform another master adjustment, etc.

In the examples of FIGS. 8A-8B, the electrodes within a particular ring (e.g., electrodes represented by indicators 858B-1 and 858B-3 within the first ring or electrodes 4 represented by indicators 858C-1 and 858C-3 within the second ring) have the same therapy parameter value (e.g., 0.2 milliamps for indicators 858B-1 and 858B-3 and 0.5 milliamps for indicators 858C-1 and 858C-3). This relationship is provided for example only. In other examples not expressly depicted in FIGS. 8A-8B, each electrode 48 of each ring may have a different value for the same therapy parameter. Furthermore, in the foregoing examples, the user may "lock" all of electrodes 48. In other examples not expressly depicted herein, user interface 800 may allow the user to lock separate levels (or rings) of electrodes 48 (e.g., a level 858A lock, a level 858B lock, a level 858C lock, and/or a level 858D lock) alternatively or in addition to allowing the user to lock all of electrodes 48.

In the example of FIGS. 8A-8B, external programmer 40 performs a master adjustment to increase each value of the therapy parameters of each of electrodes corresponding to electrode icons 848B-1, 848B-3, 848C-1, and 848C-3 by an amount specified by the relationship to maintain the ratio of the value of the therapy parameter of each of the electrodes 48 corresponding to electrode icons 848B-1, 848B-3, 848C-1, and 848C-3 to one another. However, in other examples, external programmer 40 may perform a master adjustment to decrease each value of the therapy parameters of each of the selected electrodes 48 by an amount specified by the relationship to maintain the ratio of the value of the therapy parameter of each of the selected electrodes 48 to one another. Furthermore, in the example of FIGS. 8A-8B, the adjusted therapy parameter is a current amplitude of the selected electrodes 48. However, in other examples, therapy parameters other than current amplitude may be used, such as one of a voltage amplitude or a current amplitude, an electrical stimulation pulse width, an electrical stimulation pulse count, a duty cycle of the electrical stimulation, an electrical stimulation pulse rate or a frequency of the electrical stimulation, etc.

The software user interface design described herein support the new programming capabilities of independent electrode control (IEC) and directional programming. IEC allows different stimulation amplitudes within the same program and the directional programming is achieved by the lead's segmented electrode configuration.

In some examples, user interface 800 may operate in the following modes and configurations:

Electrode Selection Mode. When the user is selecting electrode configuration on the lead, stimulation is locked.

Stimulation Mode. When the user has updated their electrode configuration and the stimulation controls are available.

Level Configuration. When no single segment differs from other electrodes on its level.

Level Mode. When new UI elements are in their level mode display.

Segment Configuration. Refers to any configuration where any segmented level has a combination of activated and deactivated electrodes, or has more than one amplitude value.

Segment Mode. When new UI elements are in the segment mode display.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method comprising:
   receiving, by processing circuitry and via a lock button presented in a user interface, user input requesting a relationship of first values of a therapy parameter to be locked for multiple electrodes of a plurality of electrodes;
   receiving, by the processing circuitry, the first values of the therapy parameter for each respective electrode of the multiple electrodes;
   defining, by the processing circuitry and based on the first values, the relationship for the multiple electrodes of the plurality of electrodes, wherein the relationship defines a ratio of the first values of the therapy parameter between the multiple electrodes;
   performing, by the processing circuitry, a master adjustment that adjusts each first value of the therapy parameter for each respective electrode of the multiple electrodes by an amount specified by the relationship to determine second values of the therapy parameter for each respective electrode that maintains the ratio of the first values of the therapy parameter between the multiple electrodes; and
   controlling, by the processing circuitry, delivery of electrical stimulation according to the second values of the therapy parameter for each respective electrode.

2. The method of claim 1,
   wherein the relationship further defines a shape of an electrical field produced by the electrical stimulation delivered according to each value of the therapy parameter of the multiple electrodes, and
   wherein performing the master adjustment comprises performing the master adjustment that adjusts each value of the therapy parameter of each respective electrode of the multiple electrodes by the amount specified by the relationship so as to adjust a volume of tissue of the patient activated by the electrical stimulation while maintaining the shape of the electrical field produced by the electrical stimulation.

3. The method of claim 1, wherein performing the master adjustment that adjusts each value of the therapy parameter for each respective electrode of the multiple electrodes by the amount specified by the relationship comprises increasing each value of the therapy parameter for each respective electrode of the multiple electrodes by the amount specified by the relationship to maintain the ratio of the value of the therapy parameter between the multiple electrodes.

4. The method of claim 1, wherein performing the master adjustment that adjusts each value of the therapy parameter for each respective electrode of the multiple electrodes by the amount specified by the relationship comprises decreasing each value of the therapy parameter for each respective electrode of the multiple electrodes by the amount specified by the relationship to maintain the ratio of the value of the therapy parameter between the multiple electrodes.

5. The method of claim 1, wherein performing the master adjustment comprises performing the master adjustment in response to receiving, via the user interface, an input requesting the master adjustment.

6. The method of claim 1, wherein the method further comprises:
   receiving, by the processing circuitry and via the user interface, a first input specifying a selection of the multiple electrodes of the plurality of electrodes; and
   receiving, by the processing circuitry and via the user interface, a second input specifying the first values of the therapy parameters of the multiple electrodes,
   wherein defining the relationship for the multiple electrodes of the plurality of electrodes comprises defining the relationship for the multiple electrodes of the plurality of electrodes in response to receiving, via the user interface, the user input requesting to lock the relationship, and
   wherein performing the master adjustment comprises performing the master adjustment in response to receiving, via the user interface, a fourth input specifying the master adjustment.

7. The method of claim 6, further comprising:
   receiving, by the processing circuitry and via the lock button presented in the user interface, a fifth input to unlock the relationship;
   receiving, by the processing circuitry and via the user interface, a sixth input specifying a third value of the therapy parameter of a first electrode of the multiple electrodes; and
   performing, by the processing circuitry and in response to receiving the fifth input and the sixth input, an adjustment to adjust the second value of the therapy parameter of the first electrode to the third value without maintaining the ratio of the first values of the therapy parameter between the multiple electrodes.

8. The method of claim 1, further comprising outputting, by the processing circuitry and for display to a user:
the lock button;
a representation of the multiple electrodes of the plurality of electrodes for which the relationship is defined;
a representation of the other electrodes of the plurality of electrodes for which the relationship is not defined;
a representation of the first values of the therapy parameter of each electrode of the multiple electrodes; and
a representation of the master adjustment.

9. The method of claim 1, wherein the therapy parameter comprises one of a voltage amplitude or a current amplitude.

10. The method of claim 1, wherein the therapy parameter comprises one or more of an electrical stimulation pulse width, an electrical stimulation pulse count, or a duty cycle of the electrical stimulation.

11. The method of claim 1, wherein the therapy parameter comprises one of an electrical stimulation pulse rate or a frequency of the electrical stimulation.

12. The method of claim 1,
wherein the plurality of electrodes are disposed on a lead,
wherein the plurality of electrodes are grouped into a plurality of electrode subsets, each electrode subset comprising several electrodes disposed at different locations around a perimeter of the lead, and
wherein the multiple electrodes comprise multiple electrodes within one electrode subset of the plurality of electrode subsets.

13. The method of claim 1,
wherein the plurality of electrodes are disposed on a lead,
wherein the plurality of electrodes are grouped into a plurality of electrode subsets, each electrode subset disposed at different respective axial locations along the lead, and each electrode subset comprising several electrodes disposed at different locations around a perimeter of the lead, and
wherein the multiple electrodes comprise:
a first electrode at a first position around the perimeter of the lead and a first axial position along the lead within a first electrode subset of the plurality of electrode subsets, and
a second electrode at the first position around the perimeter of the lead and a second axial position along the lead within a second electrode subset of the plurality of electrode subsets.

14. A system comprising:
a memory; and
processing circuitry operatively coupled to the memory and configured to:
receive, via a lock button presented in a user interface, user input requesting a relationship of first values of a therapy parameter to be locked for multiple electrodes of a plurality of electrodes;
receive the first values of the therapy parameter for each respective electrode of the multiple electrodes;
define, based on the first values, the relationship for the multiple electrodes of the plurality of electrodes, wherein the relationship defines a ratio of the first values of the therapy parameter between the multiple electrodes;
perform a master adjustment that adjusts each first value of the therapy parameter for each respective electrode of the multiple electrodes by an amount specified by the relationship to determine second values of the therapy parameter for each respective electrode that maintains the ratio of the first values of the therapy parameter between the multiple electrodes; and
control delivery of electrical stimulation according to the second values of the therapy parameter for each respective electrode.

15. The system of claim 14, further comprising the plurality of electrodes disposed on a lead.

16. The system of claim 14, further comprising:
the plurality of electrodes; and
an implantable medical device configured to couple to the plurality of electrodes, wherein to control delivery of electrical stimulation according to the master adjustment, the processing circuitry is configured to control the implantable medical device to deliver, via the selected multiple electrodes, the electrical stimulation according to the master adjustment.

17. The system of claim 14, further comprising:
an external programmer that comprises the processing circuitry and the memory; and a medical device the plurality of electrodes,
wherein the external programmer is configured to control the medical device to deliver the electrical stimulation according to the master adjustment.

18. The system of claim 14,
wherein the system further comprises a display, and
wherein the processing circuitry is further configured to control the display to display the lock button configured to indicate that the relationship is locked such that the ratio of the first values of the therapy parameter between the multiple electrodes is maintained or the relationship is not locked such that the ratio of the first values of the therapy parameter between the multiple electrodes is not maintained.

19. A device comprising:
a display;
a memory; and
processing circuitry operatively coupled to the memory and configured to:
control the display to output, for display to a user, a representation of a plurality of electrodes;
receive a first input specifying a selection of multiple electrodes of the plurality of electrodes;
control the display to output, for display to the user and in response to receiving the first input, a representation of the selected multiple electrodes;
receive a second input specifying a first value of a therapy parameter of each electrode of the multiple electrodes;
control the display to output, for display to the user and in response to receiving the second input, a representation of the first value of the therapy parameter of each electrode of the multiple electrodes;
receive, via a lock button presented in a user interface, a third input requesting to lock a relationship of the first values for the selected multiple electrodes of the plurality of electrodes, wherein the relationship defines a ratio of the first values of first the therapy parameter between the multiple electrodes;
define, based on the first values of the therapy parameter of each electrode of the multiple electrodes, the relationship;
control the display to output, for display to the user and in response to receiving the third input, an indication that the relationship for the selected multiple electrodes of the plurality of electrodes is locked;

receive a fourth input specifying a master adjustment that adjusts each first value of the therapy parameter for each respective electrode of the selected multiple electrodes by an amount specified by the relationship to determine second values of the therapy parameter for each respective electrode of the selected multiple electrodes that maintains the ratio of the first values of the therapy parameter between the multiple electrodes; and control the display to output, for display to the user and in response to receiving the fourth input, a representation of the second values of the therapy parameters of the multiple electrodes according to the master adjustment.

20. The device of claim 19, wherein the processing circuitry is further configured to:

perform the master adjustment to adjust each first value of the therapy parameter for each respective electrode of the selected multiple electrodes by an amount specified by the relationship to determine the second values of the therapy parameter for each respective electrode that maintains the ratio of the first values of the therapy parameter between the multiple electrodes; and control a medical device to deliver electrical stimulation according to the second values of the therapy parameter for each respective electrode.

\* \* \* \* \*